US009545487B2

(12) United States Patent
Besseler et al.

(10) Patent No.: US 9,545,487 B2
(45) Date of Patent: Jan. 17, 2017

(54) DISPENSER WITH ENCODING MEANS

(71) Applicants: Jens Besseler, Bingen (DE); Holger Holakovsky, Witten (DE); Herbert Argauer, Pirk (DE); Josef Gatz, Moosbach (DE); Andreas Gorshoefer, Nittenau (DE)

(72) Inventors: Jens Besseler, Bingen (DE); Holger Holakovsky, Witten (DE); Herbert Argauer, Pirk (DE); Josef Gatz, Moosbach (DE); Andreas Gorshoefer, Nittenau (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 428 days.

(21) Appl. No.: 13/861,463

(22) Filed: Apr. 12, 2013

(65) Prior Publication Data

US 2013/0269687 A1  Oct. 17, 2013

(30) Foreign Application Priority Data

Apr. 13, 2012  (EP) .................................... 12164050

(51) Int. Cl.
  *A61M 11/02* (2006.01)
  *A61M 11/00* (2006.01)
  *A61M 16/20* (2006.01)

(52) U.S. Cl.
  CPC .......... *A61M 11/006* (2014.02); *A61M 11/007* (2014.02); *A61M 11/02* (2013.01);
  (Continued)

(58) Field of Classification Search
  CPC ... A61M 11/00; A61M 11/006; A61M 11/007; A61M 11/02; A61M 11/08; A61M 15/00; A61M 15/0001; A61M 15/0036; A61M 15/0038;A61M 15/004; A61M 15/0065; A61M 15/0066; A61M 15/0071; A61M 15/0073; A61M 15/0076; A61M 15/0081; A61M 15/009; A61M 16/00; A61M 16/0051; A61M 16/10; A61M 16/12; A61M 16/20; A61M 39/00; A61M 39/10; A61N 1/36003; A62B 7/00; A62B 7/10; B01F 3/04

(Continued)

(56) References Cited

U.S. PATENT DOCUMENTS

| 1,828,864 A | 10/1931 | Hopkins |
| 2,015,970 A | 10/1935 | Schoene |

(Continued)

FOREIGN PATENT DOCUMENTS

| AU | 2005201364 A1 | 7/2006 |
| CA | 1094549 A | 1/1981 |

(Continued)

OTHER PUBLICATIONS

International Search Report for PCT/EP2013/001068 mailed Jun. 5, 2013.

(Continued)

*Primary Examiner* — Annette Dixon
(74) *Attorney, Agent, or Firm* — Michael P. Morris; Mary-Ellen M. Devlin

(57) ABSTRACT

Disclosed is a nebulizer having attached housing, which is attached in a way that permits removal, which housing holds containers of liquid medication for dispensing via nebulization, which nebulizer is constructed to allow containers holding the medication to be used and held within the housing provided that such containers match or conform to the certain mechanical requirements of the nebulizer and housing.

**10 Claims, 11

(52) U.S. Cl.
CPC ......... *A61M 16/20* (2013.01); *A61M 2205/27* (2013.01); *A61M 2205/6036* (2013.01); *A61M 2205/6045* (2013.01)

(58) Field of Classification Search
USPC ..... 128/200.14, 200.17, 200.21, 200.24, 912
See application file for complete search history.

(56) References Cited

U.S. PATENT DOCUMENTS

| | | |
|---|---|---|
| 2,127,401 A | 8/1938 | Gillican |
| 2,161,071 A | 6/1939 | McGrath et al. |
| 2,321,428 A | 6/1943 | Schloz |
| 2,329,311 A | 9/1943 | Waters |
| 2,362,103 A | 11/1944 | Smith |
| 2,651,303 A | 9/1953 | Johnson et al. |
| 2,720,969 A | 10/1955 | Kendall |
| 2,793,776 A | 5/1957 | Lipari |
| 2,974,880 A | 3/1961 | Stewart et al. |
| 3,032,823 A | 5/1962 | Sherman et al. |
| 3,157,179 A | 11/1964 | Allen et al. |
| 3,172,568 A | 3/1965 | Modderno |
| 3,196,587 A | 7/1965 | Hayward et al. |
| 3,223,289 A | 12/1965 | Bouet |
| 3,299,603 A | 1/1967 | Shaw |
| 3,354,883 A | 11/1967 | Southerland |
| 3,440,144 A | 4/1969 | Anderson et al. |
| 3,457,694 A | 7/1969 | Tatibana |
| 3,491,803 A | 1/1970 | Galik |
| 3,502,035 A | 3/1970 | Fedit |
| 3,580,249 A | 5/1971 | Takaoka |
| 3,590,557 A | 7/1971 | Vogel |
| 3,632,743 A | 1/1972 | Geller et al. |
| 3,655,096 A | 4/1972 | Easter |
| 3,674,060 A | 7/1972 | Ruekberg |
| 3,675,825 A | 7/1972 | Morane |
| 3,802,604 A | 4/1974 | Morane et al. |
| 3,820,698 A | 6/1974 | Franz |
| 3,842,836 A | 10/1974 | Ogle |
| 3,858,580 A | 1/1975 | Ogle |
| 3,861,851 A | 1/1975 | Schiemann |
| 3,870,147 A | 3/1975 | Orth |
| 3,924,741 A | 12/1975 | Kachur et al. |
| 3,933,279 A | 1/1976 | Maier |
| 3,946,732 A | 3/1976 | Hurscham |
| 3,949,751 A | 4/1976 | Birch et al. |
| 3,951,310 A | 4/1976 | Steiman |
| 3,953,995 A | 5/1976 | Haswell et al. |
| 3,973,603 A | 8/1976 | Franz |
| 4,012,472 A | 3/1977 | Lindsey |
| 4,031,892 A | 6/1977 | Hurschman |
| 4,036,439 A | 7/1977 | Green |
| 4,048,997 A | 9/1977 | Raghavachari et al. |
| 4,067,499 A | 1/1978 | Cohen |
| 4,094,317 A | 6/1978 | Wasnich |
| 4,126,559 A | 11/1978 | Cooper |
| 4,153,689 A | 5/1979 | Hirai et al. |
| 4,174,035 A | 11/1979 | Wiegner |
| 4,177,938 A | 12/1979 | Brina |
| 4,178,928 A | 12/1979 | Tischlinger |
| 4,195,730 A | 4/1980 | Hunt |
| 4,245,788 A | 1/1981 | Wright |
| 4,275,840 A | 6/1981 | Staar |
| 4,315,570 A | 2/1982 | Silver et al. |
| 4,338,765 A | 7/1982 | Ohmori et al. |
| 4,377,106 A | 3/1983 | Workman et al. |
| 4,456,016 A | 6/1984 | Nowacki et al. |
| 4,467,965 A | 8/1984 | Skinner |
| 4,476,116 A | 10/1984 | Anik |
| 4,515,586 A | 5/1985 | Mendenhall et al. |
| 4,516,967 A | 5/1985 | Kopfer |
| 4,603,794 A | 8/1986 | DeFord et al. |
| 4,677,975 A | 7/1987 | Edgar et al. |
| 4,727,985 A | 3/1988 | McNeirney et al. |
| 4,749,082 A | 6/1988 | Gardiner et al. |
| 4,796,614 A | 1/1989 | Nowacki et al. |
| 4,805,377 A | 2/1989 | Carter |
| 4,813,210 A | 3/1989 | Masuda et al. |
| 4,821,923 A | 4/1989 | Skorka |
| 4,840,017 A | 6/1989 | Miller et al. |
| 4,863,720 A | 9/1989 | Burghart et al. |
| 4,868,582 A | 9/1989 | Dreinhoff |
| 4,885,164 A | 12/1989 | Thurow |
| 4,905,450 A | 3/1990 | Hansen et al. |
| 4,926,613 A | 5/1990 | Hansen |
| 4,951,661 A | 8/1990 | Sladek |
| 4,952,310 A | 8/1990 | McMahan et al. |
| 4,964,540 A | 10/1990 | Katz |
| RE33,444 E | 11/1990 | Lerner |
| 4,979,941 A | 12/1990 | Ogle, II |
| 4,982,875 A | 1/1991 | Pozzi et al. |
| 5,014,492 A | 5/1991 | Fiorini et al. |
| 5,025,957 A | 6/1991 | Ranalletta et al. |
| 5,059,187 A | 10/1991 | Sperry et al. |
| 5,060,791 A | 10/1991 | Zulauf |
| 5,067,655 A | 11/1991 | Farago et al. |
| 5,156,918 A | 10/1992 | Marks et al. |
| 5,174,366 A | 12/1992 | Nagakura et al. |
| 5,207,217 A | 5/1993 | Cocozza et al. |
| 5,230,884 A | 7/1993 | Evans et al. |
| 5,237,797 A | 8/1993 | Varlet |
| 5,246,142 A | 9/1993 | DiPalma et al. |
| 5,261,565 A | 11/1993 | Drobish et al. |
| 5,263,842 A | 11/1993 | Fealey |
| 5,271,153 A | 12/1993 | Reiboldt et al. |
| 5,282,304 A | 2/1994 | Reiboldt et al. |
| 5,282,549 A | 2/1994 | Scholz et al. |
| 5,284,133 A | 2/1994 | Burns et al. |
| 5,289,948 A | 3/1994 | Moss et al. |
| 5,339,990 A | 8/1994 | Wilder |
| 5,352,196 A | 10/1994 | Haber et al. |
| 5,380,281 A | 1/1995 | Tomellini et al. |
| 5,385,140 A | 1/1995 | Smith |
| 5,394,866 A | 3/1995 | Ritson et al. |
| 5,408,994 A | 4/1995 | Wass et al. |
| 5,433,343 A | 7/1995 | Meshberg |
| 5,435,282 A | 7/1995 | Haber et al. |
| 5,435,884 A | 7/1995 | Simmons et al. |
| 5,451,569 A | 9/1995 | Wong et al. |
| 5,456,522 A | 10/1995 | Beach |
| 5,456,533 A | 10/1995 | Streiff et al. |
| 5,472,143 A | 12/1995 | Bartels et al. |
| 5,482,030 A | 1/1996 | Klein |
| 5,487,378 A | 1/1996 | Robertson et al. |
| 5,497,944 A | 3/1996 | Weston et al. |
| 5,499,750 A | 3/1996 | Manifold |
| 5,499,751 A | 3/1996 | Meyer |
| 5,503,869 A | 4/1996 | Van Oort |
| 5,509,404 A | 4/1996 | Lloyd et al. |
| 5,518,147 A | 5/1996 | Peterson et al. |
| 5,533,994 A | 7/1996 | Meyer |
| 5,541,569 A | 7/1996 | Jang |
| 5,544,646 A | 8/1996 | Lloyd et al. |
| 5,547,094 A | 8/1996 | Bartels et al. |
| 5,569,191 A | 10/1996 | Meyer |
| 5,574,006 A | 11/1996 | Yanagawa |
| 5,579,760 A | 12/1996 | Kohler |
| 5,593,069 A | 1/1997 | Jinks |
| 5,599,297 A | 2/1997 | Chin et al. |
| 5,603,943 A | 2/1997 | Yanagawa |
| 5,614,172 A | 3/1997 | Geimer |
| 5,622,162 A | 4/1997 | Johansson et al. |
| 5,622,163 A | 4/1997 | Jewett et al. |
| 5,643,868 A | 7/1997 | Weiner et al. |
| 5,662,098 A | 9/1997 | Yoshida |
| 5,662,271 A | 9/1997 | Weston et al. |
| 5,676,930 A | 10/1997 | Jager et al. |
| 5,685,846 A | 11/1997 | Michaels, Jr. |
| 5,697,242 A | 12/1997 | Halasz et al. |
| 5,709,202 A | 1/1998 | Lloyd et al. |
| 5,722,598 A | 3/1998 | Werding |
| 5,738,087 A | 4/1998 | King |
| 5,740,967 A | 4/1998 | Simmons et al. |
| 5,763,396 A | 6/1998 | Weiner et al. |
| 5,775,321 A | 7/1998 | Alband |

(56) References Cited

U.S. PATENT DOCUMENTS

| | | |
|---|---|---|
| 5,782,345 A | 7/1998 | Guasch et al. |
| 5,827,262 A | 10/1998 | Neftel et al. |
| 5,829,435 A | 11/1998 | Rubsamen et al. |
| 5,833,088 A | 11/1998 | Kladders et al. |
| 5,848,588 A | 12/1998 | Foley et al. |
| 5,868,287 A | 2/1999 | Kurokawa et al. |
| 5,881,718 A | 3/1999 | Mortensen et al. |
| 5,884,620 A | 3/1999 | Gonda et al. |
| 5,902,298 A | 5/1999 | Niedospial, Jr. et al. |
| 5,934,272 A | 8/1999 | Lloyd et al. |
| 5,935,101 A | 8/1999 | Kato et al. |
| 5,941,244 A | 8/1999 | Yamazaki et al. |
| 5,950,016 A | 9/1999 | Tanaka |
| 5,950,403 A | 9/1999 | Yamaguchi et al. |
| 5,951,882 A | 9/1999 | Simmons et al. |
| 5,964,416 A | 10/1999 | Jaeger et al. |
| 5,975,370 A | 11/1999 | Durliat |
| 5,997,263 A | 12/1999 | Van Lintel et al. |
| 6,041,969 A | 3/2000 | Parise |
| 6,053,368 A | 4/2000 | Geimer |
| 6,062,430 A | 5/2000 | Fuchs |
| 6,098,618 A | 8/2000 | Jennings et al. |
| 6,110,247 A | 8/2000 | Birmingham et al. |
| 6,116,233 A | 9/2000 | Denyer et al. |
| 6,119,853 A | 9/2000 | Garrill et al. |
| 6,120,492 A | 9/2000 | Finch et al. |
| 6,123,068 A | 9/2000 | Lloyd et al. |
| 6,131,566 A | 10/2000 | Ashurst et al. |
| 6,145,703 A | 11/2000 | Opperman |
| 6,149,054 A | 11/2000 | Cirrillo et al. |
| 6,152,296 A | 11/2000 | Shih |
| 6,171,972 B1 | 1/2001 | Mehregany et al. |
| 6,176,442 B1 | 1/2001 | Eicher et al. |
| 6,179,118 B1 | 1/2001 | Garrill et al. |
| 6,186,409 B1 | 2/2001 | Srinath et al. |
| 6,199,766 B1 | 3/2001 | Fox et al. |
| 6,223,933 B1 | 5/2001 | Hochrainer et al. |
| 6,224,568 B1 | 5/2001 | Morimoto et al. |
| 6,237,589 B1 | 5/2001 | Denyer et al. |
| 6,259,654 B1 | 7/2001 | de la Huerga |
| 6,267,154 B1 | 7/2001 | Felicelli et al. |
| 6,279,786 B1 | 8/2001 | de Pous et al. |
| 6,302,101 B1 | 10/2001 | Py |
| 6,315,173 B1 | 11/2001 | Di Giovanni et al. |
| 6,319,943 B1 | 11/2001 | Joshi et al. |
| 6,341,718 B1 | 1/2002 | Schilthuizen et al. |
| 6,349,856 B1 | 2/2002 | Chastel |
| 6,352,152 B1 | 3/2002 | Anderson et al. |
| 6,352,181 B1 | 3/2002 | Eberhard et al. |
| 6,363,932 B1 | 4/2002 | Forchione et al. |
| 6,375,048 B1 | 4/2002 | van der Meer et al. |
| 6,392,962 B1 | 5/2002 | Wyatt |
| 6,395,331 B1 | 5/2002 | Yan et al. |
| 6,401,710 B1 | 6/2002 | Scheuch et al. |
| 6,401,987 B1 | 6/2002 | Oechsel et al. |
| 6,402,055 B1 | 6/2002 | Jaeger et al. |
| 6,405,872 B1 | 6/2002 | Ruther et al. |
| 6,412,659 B1 | 7/2002 | Kneer |
| 6,419,167 B1 | 7/2002 | Fuchs |
| 6,423,298 B2 | 7/2002 | McNamara et al. |
| 6,427,682 B1 | 8/2002 | Klimowicz et al. |
| 6,457,658 B2 | 10/2002 | Srinath et al. |
| 6,464,108 B2 | 10/2002 | Corba |
| 6,481,435 B2 | 11/2002 | Hochrainer et al. |
| 6,491,897 B1 | 12/2002 | Freund et al. |
| 6,503,362 B1 | 1/2003 | Bartels et al. |
| 6,513,519 B2 | 2/2003 | Gallem |
| 6,543,448 B2 | 4/2003 | Smith et al. |
| 6,548,647 B2 | 4/2003 | Dietz et al. |
| 6,550,477 B1 | 4/2003 | Casper et al. |
| 6,565,743 B1 | 5/2003 | Poirier et al. |
| 6,578,741 B2 | 6/2003 | Ritsche et al. |
| 6,581,596 B1 | 6/2003 | Truitt et al. |
| 6,584,976 B2 | 7/2003 | Japuntich et al. |
| 6,606,990 B2 | 8/2003 | Stapleton et al. |
| 6,620,438 B2 | 9/2003 | Pairet et al. |
| 6,626,309 B1 | 9/2003 | Jansen et al. |
| 6,640,805 B2 | 11/2003 | Castro et al. |
| 6,641,782 B1 | 11/2003 | Mauchan et al. |
| 6,669,176 B2 | 12/2003 | Rock |
| 6,679,254 B1 | 1/2004 | Rand et al. |
| 6,685,691 B1 | 2/2004 | Freund et al. |
| 6,698,421 B2 | 3/2004 | Attolini |
| 6,706,726 B2 | 3/2004 | Meissner et al. |
| 6,708,846 B1 | 3/2004 | Fuchs et al. |
| 6,725,858 B2 | 4/2004 | Loescher |
| 6,729,328 B2 | 5/2004 | Goldemann |
| 6,732,731 B1 | 5/2004 | Tseng |
| 6,745,763 B2 | 6/2004 | Webb |
| 6,779,520 B2 | 8/2004 | Genova et al. |
| 6,789,702 B2 | 9/2004 | O'Connor et al. |
| 6,792,945 B2 | 9/2004 | Davies et al. |
| 6,823,862 B2 | 11/2004 | McNaughton |
| 6,825,441 B2 | 11/2004 | Katooka et al. |
| 6,846,413 B1 | 1/2005 | Kadel et al. |
| 6,866,039 B1 | 3/2005 | Wright et al. |
| 6,889,690 B2 | 5/2005 | Crowder et al. |
| 6,890,517 B2 | 5/2005 | Drechsel et al. |
| 6,915,901 B2 | 7/2005 | Feinberg et al. |
| 6,929,004 B1 | 8/2005 | Bonney et al. |
| 6,932,962 B1 | 8/2005 | Backstrom et al. |
| 6,942,127 B2 | 9/2005 | Raats |
| 6,964,759 B2 | 11/2005 | Lewis et al. |
| 6,977,042 B2 | 12/2005 | Kadel et al. |
| 6,978,916 B2 | 12/2005 | Smith |
| 6,986,346 B2 | 1/2006 | Hochrainer et al. |
| 6,988,496 B1 | 1/2006 | Eicher et al. |
| 6,994,083 B2 | 2/2006 | Foley et al. |
| 7,040,311 B2 | 5/2006 | Hochrainer et al. |
| 7,066,408 B2 | 6/2006 | Sugimoto et al. |
| 7,090,093 B2 | 8/2006 | Hochrainer et al. |
| 7,131,441 B1 | 11/2006 | Keller et al. |
| 7,258,716 B2 | 8/2007 | Shekarriz et al. |
| 7,314,187 B2 | 1/2008 | Hochrainer et al. |
| 7,331,340 B2 | 2/2008 | Barney |
| 7,341,208 B2 | 3/2008 | Peters et al. |
| 7,380,575 B2 | 6/2008 | Stricklin |
| 7,417,051 B2 | 8/2008 | Banholzer et al. |
| 7,451,876 B2 | 11/2008 | Bossi et al. |
| 7,470,422 B2 | 12/2008 | Freund et al. |
| 7,556,037 B2 | 7/2009 | Klein |
| 7,559,597 B2 | 7/2009 | Mori |
| 7,571,722 B2 | 8/2009 | Wuttke et al. |
| 7,579,358 B2 | 8/2009 | Boeck et al. |
| 7,611,694 B2 | 11/2009 | Schmidt |
| 7,611,709 B2 | 11/2009 | Bassarab et al. |
| 7,621,266 B2 | 11/2009 | Kladders et al. |
| 7,645,383 B2 | 1/2010 | Kadel et al. |
| 7,652,030 B2 | 1/2010 | Moesgaard et al. |
| 7,665,461 B2 * | 2/2010 | Zierenberg et al. ..... 128/200.21 |
| 7,681,811 B2 | 3/2010 | Geser et al. |
| 7,686,014 B2 | 3/2010 | Boehm et al. |
| 7,717,299 B2 | 5/2010 | Greiner-Perth |
| 7,723,306 B2 | 5/2010 | Bassarab et al. |
| 7,743,945 B2 | 6/2010 | Lu et al. |
| 7,779,838 B2 | 8/2010 | Hetzer et al. |
| 7,802,568 B2 | 9/2010 | Eicher et al. |
| 7,819,342 B2 | 10/2010 | Spallek et al. |
| 7,823,584 B2 | 11/2010 | Geser et al. |
| 7,837,235 B2 | 11/2010 | Geser et al. |
| 7,849,851 B2 | 12/2010 | Zierenberg et al. |
| 7,896,264 B2 | 3/2011 | Eicher et al. |
| 7,980,243 B2 | 7/2011 | Hochrainer |
| 7,994,188 B2 | 8/2011 | Disse |
| 8,062,626 B2 | 11/2011 | Freund et al. |
| 8,167,171 B2 | 5/2012 | Moretti |
| 8,479,725 B2 | 7/2013 | Hausmann et al. |
| 8,495,901 B2 | 7/2013 | Hahn et al. |
| 8,650,840 B2 | 2/2014 | Holakovsky et al. |
| 8,651,338 B2 | 2/2014 | Leak et al. |
| 8,656,910 B2 | 2/2014 | Boeck et al. |
| 8,733,341 B2 | 5/2014 | Boeck et al. |
| 8,734,392 B2 | 5/2014 | Stadelhofer |
| 8,950,393 B2 * | 2/2015 | Holakovsky et al. ... 128/200.14 |

(56) References Cited

U.S. PATENT DOCUMENTS

| | | |
|---|---|---|
| 8,960,188 B2 | 2/2015 | Bach et al. |
| 9,027,854 B2 | 5/2015 | Moser et al. |
| 9,192,734 B2 | 11/2015 | Hausmann et al. |
| 9,238,031 B2 | 1/2016 | Schmelzer et al. |
| 2001/0008632 A1 | 7/2001 | Freund et al. |
| 2001/0028308 A1 | 10/2001 | De La Huerga |
| 2001/0032643 A1 | 10/2001 | Hochrainer et al. |
| 2001/0035182 A1 | 11/2001 | Rubin et al. |
| 2002/0000225 A1 | 1/2002 | Schuler et al. |
| 2002/0007155 A1 | 1/2002 | Freund et al. |
| 2002/0046751 A1 | 4/2002 | MacRae et al. |
| 2002/0060255 A1 | 5/2002 | Benoist |
| 2002/0074429 A1 | 6/2002 | Hettrich et al. |
| 2002/0079285 A1 | 6/2002 | Jansen et al. |
| 2002/0092523 A1 | 7/2002 | Connelly et al. |
| 2002/0111363 A1 | 8/2002 | Drechsel et al. |
| 2002/0129812 A1 | 9/2002 | Litherland et al. |
| 2002/0137764 A1 | 9/2002 | Drechsel et al. |
| 2002/0176788 A1 | 11/2002 | Moutafis et al. |
| 2003/0039915 A1 | 2/2003 | Holt et al. |
| 2003/0064032 A1 | 4/2003 | Lamche et al. |
| 2003/0066524 A1 | 4/2003 | Hochrainer et al. |
| 2003/0085254 A1 | 5/2003 | Katooka et al. |
| 2003/0098023 A1 | 5/2003 | Drachmann et al. |
| 2003/0106827 A1 | 6/2003 | Cheu et al. |
| 2003/0145849 A1 | 8/2003 | Drinan et al. |
| 2003/0178020 A1 | 9/2003 | Scarrott |
| 2003/0181478 A1 | 9/2003 | Drechsel et al. |
| 2003/0187387 A1 | 10/2003 | Wirt et al. |
| 2003/0191151 A1 | 10/2003 | Chaudry et al. |
| 2003/0194379 A1 | 10/2003 | Brugger et al. |
| 2003/0209238 A1 | 11/2003 | Peters et al. |
| 2003/0226907 A1 | 12/2003 | Geser et al. |
| 2004/0004138 A1 | 1/2004 | Hettrich et al. |
| 2004/0010239 A1 | 1/2004 | Hochrainer et al. |
| 2004/0015126 A1 | 1/2004 | Zierenberg et al. |
| 2004/0019073 A1 | 1/2004 | Drechsel et al. |
| 2004/0055907 A1 | 3/2004 | Marco |
| 2004/0060476 A1 | 4/2004 | Sirejacob |
| 2004/0069799 A1 | 4/2004 | Gee et al. |
| 2004/0092428 A1 | 5/2004 | Chen et al. |
| 2004/0094147 A1 | 5/2004 | Schyra et al. |
| 2004/0134494 A1 | 7/2004 | Papania et al. |
| 2004/0134824 A1 | 7/2004 | Chan et al. |
| 2004/0139700 A1 | 7/2004 | Powell et al. |
| 2004/0143235 A1 | 7/2004 | Freund et al. |
| 2004/0166065 A1 | 8/2004 | Schmidt |
| 2004/0182867 A1 | 9/2004 | Hochrainer et al. |
| 2004/0184994 A1 | 9/2004 | DeStefano et al. |
| 2004/0194524 A1 | 10/2004 | Jentzsch |
| 2004/0231667 A1 | 11/2004 | Horton et al. |
| 2005/0028815 A1 | 2/2005 | Deaton et al. |
| 2005/0028816 A1* | 2/2005 | Fishman et al. ......... 128/200.24 |
| 2005/0061314 A1 | 3/2005 | Davies et al. |
| 2005/0089478 A1 | 4/2005 | Govind et al. |
| 2005/0098172 A1 | 5/2005 | Anderson |
| 2005/0126469 A1 | 6/2005 | Lu |
| 2005/0131357 A1 | 6/2005 | Denton et al. |
| 2005/0158394 A1 | 7/2005 | Staniforth et al. |
| 2005/0159441 A1 | 7/2005 | Hochrainer et al. |
| 2005/0183718 A1 | 8/2005 | Wuttke et al. |
| 2005/0191246 A1 | 9/2005 | Bechtold-Peters et al. |
| 2005/0194472 A1 | 9/2005 | Geser et al. |
| 2005/0239778 A1 | 10/2005 | Konetzki et al. |
| 2005/0247305 A1 | 11/2005 | Zierenberg et al. |
| 2005/0250704 A1 | 11/2005 | Bassarab et al. |
| 2005/0250705 A1 | 11/2005 | Bassarab et al. |
| 2005/0255119 A1 | 11/2005 | Bassarab et al. |
| 2005/0263618 A1 | 12/2005 | Spallek et al. |
| 2005/0268909 A1 | 12/2005 | Bonney et al. |
| 2005/0268915 A1 | 12/2005 | Wassenaar et al. |
| 2005/0269359 A1 | 12/2005 | Raats |
| 2006/0002863 A1 | 1/2006 | Schmelzer et al. |
| 2006/0016449 A1 | 1/2006 | Eicher et al. |
| 2006/0035874 A1 | 2/2006 | Lulla et al. |
| 2006/0037612 A1 | 2/2006 | Herder et al. |
| 2006/0067952 A1 | 3/2006 | Chen |
| 2006/0086828 A1 | 4/2006 | Bougamont et al. |
| 2006/0150971 A1 | 7/2006 | Lee et al. |
| 2006/0196500 A1 | 9/2006 | Hochrainer et al. |
| 2006/0225734 A1 | 10/2006 | Sagaser et al. |
| 2006/0239930 A1 | 10/2006 | Lamche et al. |
| 2006/0279588 A1 | 12/2006 | Yearworth et al. |
| 2006/0282045 A1 | 12/2006 | Wilkinson et al. |
| 2006/0285987 A1 | 12/2006 | Jaeger et al. |
| 2006/0289002 A1 | 12/2006 | Hetzer et al. |
| 2006/0293293 A1 | 12/2006 | Muller et al. |
| 2007/0062518 A1 | 3/2007 | Geser et al. |
| 2007/0062519 A1 | 3/2007 | Wuttke et al. |
| 2007/0062979 A1 | 3/2007 | Dunne |
| 2007/0090205 A1 | 4/2007 | Kunze et al. |
| 2007/0090576 A1 | 4/2007 | Geser et al. |
| 2007/0107720 A1 | 5/2007 | Boeck et al. |
| 2007/0119449 A1 | 5/2007 | Boehm et al. |
| 2007/0137643 A1 | 6/2007 | Bonney et al. |
| 2007/0163574 A1 | 7/2007 | Rohrschneider et al. |
| 2007/0183982 A1 | 8/2007 | Berkel et al. |
| 2007/0210121 A1 | 9/2007 | Stadelhofer et al. |
| 2007/0221211 A1 | 9/2007 | Sagalovich |
| 2007/0272763 A1 | 11/2007 | Dunne et al. |
| 2007/0298116 A1 | 12/2007 | Bechtold-Peters et al. |
| 2008/0017192 A1 | 1/2008 | Southby et al. |
| 2008/0029085 A1 | 2/2008 | Lawrence et al. |
| 2008/0083408 A1 | 4/2008 | Hodson et al. |
| 2008/0092885 A1 | 4/2008 | von Schuckmann |
| 2008/0197045 A1 | 8/2008 | Metzger et al. |
| 2008/0249459 A1 | 10/2008 | Godfrey et al. |
| 2008/0265198 A1 | 10/2008 | Warby |
| 2008/0283553 A1 | 11/2008 | Cox et al. |
| 2008/0308580 A1 | 12/2008 | Gaydos et al. |
| 2009/0032427 A1 | 2/2009 | Cheu et al. |
| 2009/0060764 A1 | 3/2009 | Mitzlaff et al. |
| 2009/0075990 A1 | 3/2009 | Schmidt |
| 2009/0114215 A1 | 5/2009 | Boeck et al. |
| 2009/0166379 A1 | 7/2009 | Wright et al. |
| 2009/0170839 A1 | 7/2009 | Schmidt |
| 2009/0185983 A1 | 7/2009 | Freund et al. |
| 2009/0197841 A1 | 8/2009 | Kreher et al. |
| 2009/0202447 A1 | 8/2009 | Kreher et al. |
| 2009/0221626 A1 | 9/2009 | Schmidt |
| 2009/0235924 A1 | 9/2009 | Holakovsky et al. |
| 2009/0272664 A1 | 11/2009 | Marshall et al. |
| 2009/0293870 A1 | 12/2009 | Brunnberg et al. |
| 2009/0306065 A1 | 12/2009 | Schmidt |
| 2009/0308772 A1 | 12/2009 | Abrams |
| 2009/0314287 A1 | 12/2009 | Spallek et al. |
| 2009/0317337 A1 | 12/2009 | Schmidt |
| 2010/0018524 A1 | 1/2010 | Jinks et al. |
| 2010/0018997 A1 | 1/2010 | Faneca Llesera |
| 2010/0044393 A1 | 2/2010 | Moretti |
| 2010/0056559 A1 | 3/2010 | Schmelzer et al. |
| 2010/0084531 A1 | 4/2010 | Schuchman |
| 2010/0095957 A1 | 4/2010 | Corbacho |
| 2010/0144784 A1 | 6/2010 | Schmelzer et al. |
| 2010/0168710 A1 | 7/2010 | Braithwaite |
| 2010/0237102 A1 | 9/2010 | Margheritis |
| 2010/0242557 A1 | 9/2010 | Spreitzer et al. |
| 2010/0242954 A1 | 9/2010 | Hahn et al. |
| 2011/0005517 A1 | 1/2011 | Boeck et al. |
| 2011/0041842 A1 | 2/2011 | Bradshaw et al. |
| 2011/0168175 A1 | 7/2011 | Dunne et al. |
| 2011/0239594 A1 | 10/2011 | Nottingham et al. |
| 2011/0268668 A1 | 11/2011 | Lamche et al. |
| 2011/0277753 A1 | 11/2011 | Dunne et al. |
| 2011/0290239 A1 | 12/2011 | Bach et al. |
| 2011/0290242 A1 | 12/2011 | Bach et al. |
| 2011/0290243 A1 | 12/2011 | Bach et al. |
| 2012/0090603 A1 | 4/2012 | Dunne et al. |
| 2012/0132199 A1 | 5/2012 | Kiesewetter |
| 2012/0138049 A1 | 6/2012 | Wachtel |
| 2012/0138713 A1 | 6/2012 | Schuy et al. |
| 2012/0260913 A1 | 10/2012 | Bach et al. |
| 2012/0325204 A1 | 12/2012 | Holakovsky et al. |
| 2013/0012908 A1 | 1/2013 | Yeung |

(56) References Cited

U.S. PATENT DOCUMENTS

| | | | |
|---|---|---|---|
| 2013/0056888 A1 | 3/2013 | Holakovsky et al. |
| 2013/0125880 A1 | 5/2013 | Holakovsky et al. |
| 2013/0125881 A1 | 5/2013 | Holakovsky et al. |
| 2013/0126389 A1 | 5/2013 | Holakovsky et al. |
| 2013/0206136 A1 | 8/2013 | Herrmann et al. |
| 2013/0269687 A1 | 10/2013 | Besseler et al. |
| 2014/0121234 A1 | 5/2014 | Kreher et al. |
| 2014/0190472 A1 | 7/2014 | Holakovsky et al. |
| 2014/0228397 A1 | 8/2014 | Schmelzer et al. |
| 2014/0331994 A1 | 11/2014 | Holakovsky et al. |
| 2015/0040890 A1 | 2/2015 | Besseler et al. |
| 2015/0040893 A1 | 2/2015 | Besseler et al. |
| 2015/0041558 A1 | 2/2015 | Besseler et al. |
| 2015/0114387 A1 | 4/2015 | Bach et al. |
| 2015/0122247 A1 | 5/2015 | Besseler et al. |
| 2015/0258021 A1 | 9/2015 | Kreher et al. |
| 2015/0306685 A1 | 10/2015 | Schmelzer et al. |
| 2015/0320947 A1 | 11/2015 | Eicher et al. |
| 2015/0320948 A1 | 11/2015 | Eicher et al. |
| 2016/0095992 A1 | 4/2016 | Wachtel |

FOREIGN PATENT DOCUMENTS

| | | |
|---|---|---|
| CA | 2233981 A1 | 4/1997 |
| CA | 2237853 A1 | 6/1997 |
| CA | 2251828 A1 | 10/1997 |
| CA | 2275392 A1 | 7/1998 |
| CA | 2297174 A1 | 2/1999 |
| CA | 2343123 A1 | 4/2000 |
| CA | 2434872 A1 | 8/2002 |
| CA | 2497680 A1 | 3/2004 |
| CA | 2513167 A1 | 10/2004 |
| CA | 2557020 A1 | 9/2005 |
| CA | 2653183 A1 | 12/2007 |
| CA | 2653422 A1 | 12/2007 |
| CN | 1125426 A | 6/1996 |
| CN | 1849174 A | 10/2006 |
| CN | 101247897 A | 8/2008 |
| DE | 1653651 A1 | 7/1971 |
| DE | 2754100 A1 | 6/1978 |
| DE | 4117078 A1 | 11/1992 |
| DE | 19625027 A1 | 1/1997 |
| DE | 19615422 A1 | 11/1997 |
| DE | 19653969 A1 | 6/1998 |
| DE | 19902844 C1 | 11/1999 |
| DE | 10007591 A1 | 11/2000 |
| DE | 10104367 A1 | 8/2002 |
| DE | 10300983 A1 | 7/2004 |
| DE | 102004031673 A1 | 1/2006 |
| DE | 202006017793 U1 | 1/2007 |
| DE | 01102006025871 A1 | 12/2007 |
| DK | 83175 C | 7/1957 |
| DK | 140801 B | 11/1979 |
| EP | 0018609 A1 | 11/1980 |
| EP | 0289336 A2 | 11/1988 |
| EP | 0354507 A2 | 2/1990 |
| EP | 0364235 A1 | 4/1990 |
| EP | 0372777 A2 | 6/1990 |
| EP | 0386800 A1 | 9/1990 |
| EP | 0412524 A1 | 2/1991 |
| EP | 0505123 A1 | 9/1992 |
| EP | 0520571 A1 | 12/1992 |
| EP | 0622311 A2 | 11/1994 |
| EP | 0642992 A2 | 3/1995 |
| EP | 0679443 A1 | 11/1995 |
| EP | 0735048 A1 | 10/1996 |
| EP | 0778221 A1 | 6/1997 |
| EP | 0845253 A2 | 6/1998 |
| EP | 0845265 A1 | 6/1998 |
| EP | 0860210 A2 | 8/1998 |
| EP | 0289332 A1 | 11/1998 |
| EP | 0916428 A2 | 5/1999 |
| EP | 0965355 A2 | 12/1999 |
| EP | 0970751 A2 | 1/2000 |
| EP | 1003478 A1 | 5/2000 |
| EP | 1017469 A1 | 7/2000 |
| EP | 1025923 A1 | 8/2000 |
| EP | 1068906 A2 | 1/2001 |
| EP | 1075875 A2 | 2/2001 |
| EP | 1092447 A2 | 4/2001 |
| EP | 1157689 A1 | 11/2001 |
| EP | 1211628 A2 | 6/2002 |
| EP | 1245244 A2 | 10/2002 |
| EP | 1312418 A2 | 5/2003 |
| EP | 1375385 A2 | 1/2004 |
| EP | 1521609 A2 | 4/2005 |
| EP | 1535643 A1 | 6/2005 |
| EP | 1595564 A1 | 11/2005 |
| EP | 1595822 A1 | 11/2005 |
| EP | 1726324 A1 | 11/2006 |
| EP | 1736193 A1 | 12/2006 |
| EP | 1795221 A1 | 6/2007 |
| EP | 1813548 A1 | 8/2007 |
| EP | 2135632 A1 | 12/2009 |
| ES | 2262348 T3 | 11/2006 |
| FR | 2505688 A1 | 11/1982 |
| FR | 2604363 A1 | 4/1988 |
| FR | 2673608 A1 | 9/1992 |
| FR | 2756502 A1 | 6/1998 |
| GB | 1524431 A | 9/1978 |
| GB | 2081396 A | 2/1982 |
| GB | 2101020 A | 1/1983 |
| GB | 2279273 A | 1/1995 |
| GB | 2291135 A | 1/1996 |
| GB | 2332372 A | 6/1999 |
| GB | 2333129 A | 7/1999 |
| GB | 2347870 A | 9/2000 |
| GB | 2355252 A | 4/2001 |
| GB | 2398253 A | 8/2004 |
| GB | 0700839.4 | 7/2008 |
| JP | S5684246 A | 7/1981 |
| JP | H01288265 A | 11/1989 |
| JP | H0228121 A | 1/1990 |
| JP | H057246 | 2/1993 |
| JP | H0553470 A | 3/1993 |
| JP | H06312019 A | 11/1994 |
| JP | H07118164 A | 5/1995 |
| JP | H07118166 A | 5/1995 |
| JP | 07323086 A | 12/1995 |
| JP | H08277226 A | 10/1996 |
| JP | H092442 A | 1/1997 |
| JP | H0977073 A | 3/1997 |
| JP | H09315953 A | 12/1997 |
| JP | 2001518428 A | 10/2001 |
| JP | 2001346878 A | 12/2001 |
| JP | 2002504411 A | 2/2002 |
| JP | 2003511212 A | 3/2003 |
| JP | 2003299717 A | 10/2003 |
| JP | 2004502502 A | 1/2004 |
| JP | 2004097617 A | 4/2004 |
| JP | 2005511210 A | 4/2005 |
| JP | 2005144459 A | 6/2005 |
| JP | 2007517529 A | 7/2007 |
| JP | 2007245144 A | 9/2007 |
| JP | 2007534379 A | 11/2007 |
| JP | 2008119489 A | 5/2008 |
| JP | 2008541808 A | 11/2008 |
| JP | 2010526620 A | 8/2010 |
| JP | 2010540371 A | 12/2010 |
| WO | 8100674 A1 | 3/1981 |
| WO | 8200785 A1 | 3/1982 |
| WO | 8300288 A1 | 2/1983 |
| WO | 8303054 A1 | 9/1983 |
| WO | 8605419 A1 | 9/1986 |
| WO | 8706137 A1 | 10/1987 |
| WO | 8803419 A1 | 5/1988 |
| WO | 8900889 A1 | 2/1989 |
| WO | 8900947 A1 | 2/1989 |
| WO | 8902279 A1 | 3/1989 |
| WO | 8903672 A1 | 5/1989 |
| WO | 8903673 A1 | 5/1989 |
| WO | 8905139 A1 | 6/1989 |
| WO | 9009780 A1 | 9/1990 |
| WO | 9009781 A1 | 9/1990 |

(56) References Cited

FOREIGN PATENT DOCUMENTS

| | | |
|---|---|---|
| WO | 9114468 A1 | 10/1991 |
| WO | 9206704 A1 | 4/1992 |
| WO | 9217231 A1 | 10/1992 |
| WO | 9221332 A1 | 12/1992 |
| WO | 9222286 | 12/1992 |
| WO | 9313737 A1 | 7/1993 |
| WO | 9324164 A1 | 12/1993 |
| WO | 9325321 A1 | 12/1993 |
| WO | 9407607 A1 | 4/1994 |
| WO | 9417822 A1 | 8/1994 |
| WO | 9425371 A1 | 11/1994 |
| WO | 9427653 A2 | 12/1994 |
| WO | 9503034 A1 | 2/1995 |
| WO | 9532015 A1 | 11/1995 |
| WO | 9600050 A1 | 1/1996 |
| WO | 9606011 A2 | 2/1996 |
| WO | 9606581 A1 | 3/1996 |
| WO | 9623522 A1 | 8/1996 |
| WO | 9701329 A1 | 1/1997 |
| WO | 9706813 A1 | 2/1997 |
| WO | 9706842 A1 | 2/1997 |
| WO | 9712683 A1 | 4/1997 |
| WO | 9712687 A1 | 4/1997 |
| WO | 9720590 A1 | 6/1997 |
| WO | 9723208 A1 | 7/1997 |
| WO | 9727804 A1 | 8/1997 |
| WO | 9735562 A1 | 10/1997 |
| WO | 9741833 A1 | 11/1997 |
| WO | 9812511 A2 | 3/1998 |
| WO | 9827959 A2 | 7/1998 |
| WO | 9831346 A1 | 7/1998 |
| WO | 9839043 A1 | 9/1998 |
| WO | 9901227 A1 | 1/1999 |
| WO | 9907340 A1 | 2/1999 |
| WO | 9911563 A1 | 3/1999 |
| WO | 9916530 A1 | 4/1999 |
| WO | 9943571 A1 | 9/1999 |
| WO | 9962495 A2 | 12/1999 |
| WO | 9965464 | 12/1999 |
| WO | 0001612 A2 | 1/2000 |
| WO | 0023037 A1 | 4/2000 |
| WO | 0023065 A2 | 4/2000 |
| WO | 0027543 A1 | 5/2000 |
| WO | 0033965 A1 | 6/2000 |
| WO | 0037336 A1 | 6/2000 |
| WO | 0049988 A2 | 8/2000 |
| WO | 0064779 A1 | 11/2000 |
| WO | 0113885 A1 | 3/2001 |
| WO | 0128489 A1 | 4/2001 |
| WO | 0164182 A2 | 9/2001 |
| WO | 0185097 A2 | 11/2001 |
| WO | 0187392 A2 | 11/2001 |
| WO | 0197888 A2 | 12/2001 |
| WO | 0198175 A1 | 12/2001 |
| WO | 0198176 A2 | 12/2001 |
| WO | 0204054 A1 | 1/2002 |
| WO | 0205879 A1 | 1/2002 |
| WO | 0217988 A2 | 3/2002 |
| WO | 0232899 A1 | 4/2002 |
| WO | 0234411 A1 | 5/2002 |
| WO | 02070141 A1 | 9/2002 |
| WO | 02089887 A1 | 11/2002 |
| WO | 03002045 A1 | 1/2003 |
| WO | 03014832 A1 | 2/2003 |
| WO | 03020253 A2 | 3/2003 |
| WO | 03022332 A2 | 3/2003 |
| WO | 03035030 A1 | 5/2003 |
| WO | 03037159 A2 | 5/2003 |
| WO | 03037259 A2 | 5/2003 |
| WO | 03049786 A2 | 6/2003 |
| WO | 03050031 A1 | 6/2003 |
| WO | 03053350 A2 | 7/2003 |
| WO | 03057593 A1 | 7/2003 |
| WO | 03059547 A1 | 7/2003 |
| WO | 03068299 A1 | 8/2003 |
| WO | 03087097 A1 | 10/2003 |
| WO | 03097139 A1 | 11/2003 |
| WO | 2004019985 A1 | 3/2004 |
| WO | 2004022052 A1 | 3/2004 |
| WO | 2004022132 A2 | 3/2004 |
| WO | 2004022244 A1 | 3/2004 |
| WO | 2004024157 A1 | 3/2004 |
| WO | 2004033954 A2 | 4/2004 |
| WO | 2004062813 A1 | 7/2004 |
| WO | 2004078236 A2 | 9/2004 |
| WO | 2004089551 A2 | 10/2004 |
| WO | 2004091704 A1 | 10/2004 |
| WO | 2004098689 A1 | 11/2004 |
| WO | 2005000476 A1 | 1/2005 |
| WO | 2005004844 A1 | 1/2005 |
| WO | 2005014175 A1 | 2/2005 |
| WO | 2005020953 A1 | 3/2005 |
| WO | 2005030211 A1 | 4/2005 |
| WO | 2005055976 A2 | 6/2005 |
| WO | 2005077445 A1 | 8/2005 |
| WO | 2005079997 A1 | 9/2005 |
| WO | 2005080001 A1 | 9/2005 |
| WO | 2005080002 A1 | 9/2005 |
| WO | 2005087299 A1 | 9/2005 |
| WO | 2005107837 A1 | 11/2005 |
| WO | 2005109948 A2 | 11/2005 |
| WO | 2005112892 A1 | 12/2005 |
| WO | 2005112996 A1 | 12/2005 |
| WO | 2005113007 A2 | 12/2005 |
| WO | 2006011638 A1 | 2/2006 |
| WO | 2006018392 A1 | 2/2006 |
| WO | 2006027595 A1 | 3/2006 |
| WO | 2006037636 A2 | 4/2006 |
| WO | 2006037948 A2 | 4/2006 |
| WO | 2006042297 A2 | 4/2006 |
| WO | 2006045813 A1 | 5/2006 |
| WO | 2006110080 A1 | 10/2006 |
| WO | 2006125577 A2 | 11/2006 |
| WO | 2006126014 A2 | 11/2006 |
| WO | 2007011475 A1 | 1/2007 |
| WO | 2007022898 A2 | 3/2007 |
| WO | 2007049239 A2 | 5/2007 |
| WO | 2007060104 A2 | 5/2007 |
| WO | 2007060105 A2 | 5/2007 |
| WO | 2007060106 A1 | 5/2007 |
| WO | 2007060107 A1 | 5/2007 |
| WO | 2007060108 A2 | 5/2007 |
| WO | 2007062721 A1 | 6/2007 |
| WO | 2007090822 A2 | 8/2007 |
| WO | 2007101557 A2 | 9/2007 |
| WO | 2007128381 A1 | 11/2007 |
| WO | 2007134965 A1 | 11/2007 |
| WO | 2007134966 A1 | 11/2007 |
| WO | 2007134967 A1 | 11/2007 |
| WO | 2007134968 A1 | 11/2007 |
| WO | 2007141201 A1 | 12/2007 |
| WO | 2007141203 A1 | 12/2007 |
| WO | 2008023017 A2 | 2/2008 |
| WO | 2008047035 A2 | 4/2008 |
| WO | 2008077623 A1 | 7/2008 |
| WO | 2008124666 A2 | 10/2008 |
| WO | 2008138936 A1 | 11/2008 |
| WO | 2008146025 A2 | 12/2008 |
| WO | 2009006137 A1 | 1/2009 |
| WO | 2009047021 A1 | 4/2009 |
| WO | 2009047173 A2 | 4/2009 |
| WO | 2009050978 A1 | 4/2009 |
| WO | 2009090245 A1 | 7/2009 |
| WO | 2009103510 A1 | 8/2009 |
| WO | 2009115200 A1 | 9/2009 |
| WO | 2010005946 A2 | 1/2010 |
| WO | 2010006870 A1 | 1/2010 |
| WO | 2010094305 A1 | 8/2010 |
| WO | 2010094413 A2 | 8/2010 |
| WO | 2010112358 A2 | 10/2010 |
| WO | 2010133294 A2 | 11/2010 |
| WO | 2011006711 A1 | 1/2011 |
| WO | 2011064160 A1 | 6/2011 |
| WO | 2011064163 A1 | 6/2011 |

(56) References Cited

FOREIGN PATENT DOCUMENTS

| WO | 2011064164 A1 | 6/2011 |
|---|---|---|
| WO | 2011131779 A1 | 10/2011 |
| WO | 2011154295 A2 | 12/2011 |
| WO | 2011160932 A1 | 12/2011 |
| WO | 2012130757 A1 | 10/2012 |
| WO | 2012159914 A1 | 11/2012 |
| WO | 2012160047 A2 | 11/2012 |
| WO | 2012160052 A1 | 11/2012 |
| WO | 2012161685 A1 | 11/2012 |
| WO | 2012162305 A1 | 11/2012 |
| WO | 2013110601 A1 | 8/2013 |
| WO | 2013152861 A1 | 10/2013 |
| WO | 2013152894 A1 | 10/2013 |
| WO | 2015018901 A1 | 2/2015 |
| WO | 2015018903 A1 | 2/2015 |
| WO | 2015018904 A1 | 2/2015 |
| WO | 2015169431 A2 | 11/2015 |
| WO | 2015169732 A1 | 11/2015 |
| ZA | 199901520 A | 12/1999 |

OTHER PUBLICATIONS

Abstract in English for WO2009050978, 2009.
"Activate". Collins English Dictionary, London: Collins, 2000, 2 pages. [Retrieved at http://search.credoreference.com/content/entry/hcengdict/activate/0 on Jun. 12, 2014].
"Lung Cancer". Merck Manual Home Edition, pp. 1-7. [Accessed at www.merck.com/mmhe/print/sec04/ch057/ch057a.html, on Jul. 28, 2010].
Abstract in English for DE19902844, 1999.
Abstract in English for DE4117078, 1992.
Abstract in English for EP0354507, 1990.
Abstract in English for FR2756502, 1998.
Abstract in English for JPS5684246, 1979.
Abstract in English of DE10007591, 2000.
Abstract in English of DE202006017793, 2007.
Abstract in English of FR2604363, Sep. 30, 1986.
Abstract in English of JPH0553470, 1993.
Abstract in English of JPH057246, 1993.
Abstract in English of JPH07118164, 1995.
Abstract in English of JPH07118166, 1995.
Abstract in English of JPH08277226, 1996.
Abstract in English of JPH092442, 1997.
Abstract in English of JPH09315953, 1997.
Abstract in English of JPH0977073, 1997.
Abstract in English of WO199706813, 1997.
Abstract in English of WO199839043, 1998.
Abstract in English of WO2002070141, 2002.
Ackermann et al.; Quantitative Online Detection of Low-Concentrated Drugs via a SERS Microfluidic System; ChemPhysChem; 2007; vol. 8; No. 18; pp. 2665-2670.
Beasley R et al: "Preservatives in Nebulizer solutions: Risks without Benefit" Pharmacotherapy, Boston, US, Bd. 18, Nr. 1, Jan. 1998.
Beasley R et al: "Preservatives in Nebulizer solutions: Risks without Benefit" Pharmacotherapy, Boston, US, Bd. 18, Nr. 1, Jan. 1998, pp. 130-139.
Bocci et al., "Pulmonary catabolism of interferons: alveolar absorption of 125I-labeled human interferon alpha is accompanied by partial loss of biological activity". Antiviral Research, vol. 4, 1984, pp. 211-220.
Chen, F-K et al., "A study of forming pressure in the tube-hydroforming process". Journal of Materials Processing Technology, 192-193, 2007, p. 404-409.

China Suppliers, Shanghai Lite Chemical Technology Co., Ltd. Product details on polyvinylpyrrolidones. Obtained online on Apr. 24, 2011.
Cras et al., "Comparison of chemical cleaning methods of glass in preparation for silanization". Biosensors & Bioelectronics, vol. 14, 1999, pp. 683-688.
Diamond et al., "Substance P Fails to Mimic Vagally Mediated Nonadrenergic Bronchodilation". Peptides, vol. 3, 1982, pp. 27-29.
Elwenspoek et al., "Silicon Micromachining", Chapter 3, Mechanical Microsensors, Springer-Verlag Berlin Heidelberg, 2001, 4 pages.
English Language Abstract of EP1068906, 2001.
Fuchs et al., "Neopterin, biochemistry and clinical use as a marker for cellular immune reactions". International Archives of Allergy and Immunology, vol. 101, No. 1, 1993, pp. 1-6, Abstract 1p.
Han et al.; Surface activation of thin silicon oxides by wet cleaning and silanization; Thin Solid Films; 2006; vol. 510; No. 1-2; pp. 175-180.
Henkel et al.; Chip modules for generation and manipulation of fluid segments for micro serial flow processes; Chemical Engineering Journal; 2004; vol. 101; pp. 439-445.
Hoffmann et al., "Mixed self-assembled monolayers (SAMs) consisting of methoxy-tri(ethylene glycol)-terminated and alkyl-terminated dimethylchlorosilanes control the non-specific adsorption of proteins at oxidic surfaces". Journal of Colloid and Interface Science, vol. 295, 2006, pp. 427-435.
Husseini et al., "Alkyl Monolayers on Silica Surfaces Prepared Using Neat, Heated Dimethylmonochlorosilanes with Low Vapor Pressures". Langmuir, vol. 19, 2003, pp. 5169-5171.
International Search Report and Written Opinion for PCT/EP2013/054324 mailed on Jun. 5, 2013.
Ip et al., "Stability of Recombinant Consensus Interferon to Air-Jet and Ultrasonic Nebulization". Journal of Pharmaceutical Sciences, vol. 84, No. 10, Oct. 1995, pp. 1210-1214.
Jendle et al., "Intrapulmonary administration of insulin to healthy volunteers". Journal of Internal Medicine, vol. 240, 1996, pp. 93-98.
JP2005144459—English language abstract only.
Kutchoukov et al., "Fabrication of nanofluidic devices using glass-to-glass anodic bonding" Sensors and Actuators A, vol. 114, 2004, pp. 521-527.
Lougheed et al., "Insulin Aggregation in Artificial Delivery Systems". Diabetologia, vol. 19, 1980, pp. 1-9.
Mandal et al., "Cytophobic surface modification of microfluidic arrays for in situ parallel peptide synthesis and cell adhesion assays". Biotechnology Progress, vol. 23, No. 4, 2007, pp. 972-978 (Author Manuscript Available in PMC, Sep. 21, 2009, 19 pages).
Niven et al., "Some Factors Associated with the Ultrasonic Nebulization of Proteins". Pharmaceutical Research, vol. 12, No. 1, 1995, pp. 53-59.
Remington Pharmacy, Editor Alfonso R. Gennaro. 19th ed., Spanish Secondary Edition: Panamericana, Spain, 1995, Sciarra, J.J., "Aerosols", pp. 2560-2582. The English translation is from the 1995 English Primary Edition, Sciarra, J.J., Chapter 95, R97-1185.
Trasch et al., "Performance data of refloquant Glucose in the Evaluation of Reflotron". Clinical Chemistry, vol. 30, 1984, p. 969 (abstract only).
Wall et al., "High levels of exopeptidase activity are present in rat and canine bronchoalveolar lavage fluid". International Journal of Pharmaceutics, vol. 97, Issue 1-3, pp. 171-181, 1993, Abstract pp. 1-2.
Wang et al.; Self-Assembled Silane Monolayers: Fabrication with Nanoscale Uniformity; Langmuir; 2005; vol. 21; No. 5; pp. 1848-1857.

* cited by examiner

PRIOR ART

PRIOR ART

DISPENSER WITH ENCODING MEANS

FIELD OF THE INVENTION

The present invention relates to a nebuliser for a fluid into which a container holding the fluid can be inserted, having a pressure generator for conveying and/or nebulising the fluid and preferably with a housing part that can be removed in order to insert the container, while coding means are provided which cooperate so that the container can only be inserted in the nebuliser or used therewith if the coding means have a matching coding. The present invention also relates to housing-like component for such a nebuliser.

BACKGROUND OF THE INVENTION

The starting point of the present invention is a nebuliser sold under the brand name "Respimat" by Boehringer Ingelheim K G, in the form of an inhaler as described in basic terms in WO 91/14468 A1 and in a specific embodiment in WO 97/12687 A1 (FIGS. 6a, 6b) and in FIGS. 1 and 2 of the appended drawings. The nebuliser comprises, as a reservoir for a fluid that is to be nebulised, an insertable container holding the fluid and a pressure generator having a drive spring for conveying and nebulising the fluid.

To supplement the disclosure of the present patent application reference is hereby made, in a precautionary capacity, to the complete disclosure of both WO 91/14468 A1 and WO 97/12687 A1. Generally, the disclosure contained therein relates preferably to a nebuliser having a spring pressure of 5 to 60 mPa, preferably 10 to 50 mPa on the fluid, with volumes per actuation of 10 to 50 µl, preferably 10 to 20 µl, most preferably about 15 µl per actuation, and particle sizes of up to 20 µm, preferably 3 to 10 µm.

Moreover, the disclosure contained therein relates preferably to a nebuliser with a cylinder-like shape and with dimensions of about 9 cm to about 15 cm in length and about 2 cm to about 5 cm in width and with a nozzle spray cone of 20° to 160°, preferably 80° to 100°. These values are deemed to be particularly preferred for the nebuliser according to the teaching of the invention as well.

By rotating an actuating member in the form of a lower housing part of the nebuliser, the drive spring can be tensioned and fluid can be aspirated into a pressure chamber of the pressure generator. After manual actuation of a blocking element, the fluid in the pressure chamber is put under pressure by the drive spring and nebulised, i.e. discharged to form an aerosol. During the tensioning on the one hand and the subsequent nebulisation on the other hand the container performs an actuating movement.

The nebuliser comprises a mechanical monitoring device which detects the rotation of the actuating member in order to count the number of actuations of the nebuliser.

In the known nebulisers, containers may be used containing different fluids, i.e. in particular different medicaments or active substances. To protect such a nebuliser and a container for such a nebuliser more effectively from a mix-up with the container during use, WO 2005/080002 A1 proposed an improved nebuliser and an improved container.

The fundamental improvement was to provide a coding so that only a specific container or a number of specific containers could be used with, in particular could be inserted in, a nebuliser intended for them. For this purpose, the nebuliser comprises first coding means, while second coding means are associated with the container. The coding means cooperate with one another such that the container with the associated second coding means can only be inserted in or used with the nebuliser when the coding means match or form a matching coding.

As this publication forms the direct starting point of the present invention that constitutes the preamble of the above-mentioned claims, to supplement the disclosure of the present patent application reference is also made, in a precautionary capacity, to the complete disclosure of this specification.

The known nebulisers, as well as the nebuliser according to the present invention, operate purely mechanically, i.e. with no propellant gas and with no electrics.

Preferably, the coding also operates and works purely mechanically so that it can be provided in a simple and inexpensive manner and with a high degree of operational reliability.

According to the prior art, the complementary coding means that are operatively connected can only ever provide a specific coding.

In order to produce a different coding, it is necessary to use different coding means, both for the nebuliser and for the housing-like component.

SUMMARY OF THE INVENTION

The present invention is based on the problem of providing a nebuliser or a housing-mounted component for such a nebuliser with improved coding options.

The invention therefore initially starts from a nebuliser for a fluid into which a container holding the fluid can be inserted, having a pressure generator for conveying and/or nebulising the fluid and preferably with a housing part that can be removed in order to insert the container, while coding means are provided which cooperate so that the container can only be inserted in the nebuliser or used therewith if the coding means have a matching coding.

It is now provided, according to the invention, that at least one of the coding means can be mounted in different defined positions such that in each position a different coding is obtained in which the coding means match one another.

The proposed solution leads to a substantially greater flexibility in terms of the generation of possible codes without the need to replace or re-design all of the coding means if it is desired to change the code. As a result, the provision of differently configured coding means can be avoided, in spite of the use of different active substances in the nebuliser, different concentrations of active substances in the fluid and/or the amount of fluid added to the container up to a certain level.

Thus with regard to the coding means the invention is moving more towards a concept of carry-over parts.

According to a first advantageous further feature of the invention it is provided that at least one of the coding means can be mounted in different defined positions on the nebuliser and at least one other of the coding means can be mounted in different defined positions or at least replaceably on the removable housing part. In this way, a comparatively large number of possible codings can be obtained while achieving a high proportion of carry-over parts.

The possibility, at least, of replacing the coding means on the removable housing part means that if there is a need for a different coding it is not necessary to reconstruct the entire removable housing part but only to replace the coding means.

According to another embodiment of the inventive concept, both the at least one coding means associated with the removable housing part and also the at least one other coding means associated with the nebuliser can be mounted in different defined positions. In this way it is possible to achieve the comparatively greatest flexibility.

At the same time, expediently, if the coding does not match, at least the container is prevented from being fully inserted, and in particular it is impossible for the fluid to make contact with the pressure generator or a conveying tube.

As already mentioned, the coding means preferably cooperate mechanically with one another, for reasons of simplicity and reliability.

The coding means can be or are mounted on the nebuliser subsequently and/or in such a way that they can be released only using a special tool. This is intended on the one hand to increase the flexibility and on the other hand to allow for handling.

The coding means are expediently mounted on the nebuliser in frictionally and/or positively locking manner, in particular by clipping, clamping or screwing.

Moreover, at least one of the coding means is configured to be at least partly in the shape of a ring, sleeve, bracket, cam, web, groove and/or hook.

According to another advantageous embodiment of the invention, it may be envisaged that the at least one coding means associated with the removable housing part is configured in the manner of part of the wall of an imaginary hollow cylinder, the wall having at least one freely passable groove extending in the direction of an axis of symmetry of the imaginary hollow cylinder, and that at least one other coding means associated with the nebuliser is provided in annular form, having at least one nose-like projection for movably engaging in the groove, the annular coding means comprising a plurality of openings on one of its end faces and a plurality of pin-like projections on an opposite end face.

Such a design has good mechanical stability.

According to another highly expedient embodiment of the inventive concept, as an additional feature, the at least one coding means associated with the removable housing part has a plurality of grooves, one groove of which is freely passable while the other grooves are rendered non-passable by transverse walls.

The transverse walls may each be embodied in particular in the manner of a frangible point.

In this way it is possible to carry out any desired coding of a coding means, configured in principle as a carry-over part, in a comparatively simple production step shortly before assembly in a nebuliser, by punching through the corresponding transverse walls of a groove accordingly.

If two coding means associated with the removable housing part and two coding means associated with the nebuliser are provided, a comparatively large number of coding combinations can be achieved while ensuring high mechanical stability.

According to another advantageous embodiment of the invention, the coding means associated with the removable housing part may comprise at least two walls each configured in the manner of part of the wall of an imaginary hollow cylinder, which are offset from one another particularly by about 180 degrees, the walls each having at least one groove extending in the direction of insertion of the container, and the walls being integrally connected to one another and the coding means associated with the nebuliser being of a sleeve-shaped configuration, while the walls of the coding means associated with the removable housing part radially surround the coding means associated with the nebuliser at least in parts and guide means for the coding means engage with one another.

In this way the variety of parts needed can be reduced and the mounting of the coding means can be simplified. At the same time, good stability of the nebuliser is ensured.

Conveniently, the coding means associated with the removable housing part can be moved into a position in which it is freely rotatable in the housing part, at least over a limited angular range, and by pushing further into the housing part can be moved into a position in which it is no longer rotatable.

This makes it possible, by simple means, to fix the coding in the manufacturing process at the latest possible point in time. The final coding can be definitively determined by simple measures (rotation, pushing further in). This ensures a very assembly-friendly coding.

Preferably, seven positions are provided into which the coding means associated with the nebuliser can be moved by rotation and further pushing into a clearly defined position which is no longer rotatable. Obviously a different number is also possible.

Similarly, the coding means associated with the nebuliser can expediently be moved into a position in which it is freely rotatable on the nebuliser at least over a limited angular range and can be moved, by pushing further onto the nebuliser, into a position in which it is no longer rotatable. In this way, the advantages mentioned above can be achieved, while in this case preferably seven selectable positions are available in which the final coding for the coding means associated with the nebuliser can be fixed.

According to another advantageous embodiment of the nebuliser according to the invention, at least two basically annular coding means are provided, each having openings or pin-like projections uniformly distributed around their circumference which respectively cooperate with pin-like projections or openings in the nebuliser or the removable housing part, respectively, while one coding means associated with the removable housing part comprises at least one projection extending in the direction of insertion of the container, and the other coding means associated with the nebuliser comprises at least one recess extending in the direction of insertion of the container, which is configured to accommodate the projection.

This embodiment of the invention allows a flexibly adjustable coding with just a few, particularly only two, coding means.

The recess and the projection may each be of rectangular configuration. Such a shape is easy to manufacture and also allows stable coding.

The removable housing part may preferably comprise an encircling groove and the projection may have a radially outwardly directed hook-like nose for engaging in the groove.

In this way, it can be very effectively ensured that the projection of the coding means associated with the removable housing part is not displaced radially inwardly, thereby interfering with the assembly of the removable housing part on the nebuliser and hence the insertion of the container.

In other words, the projection of the coding means associated with the removable housing part is thus fixed radially externally on the removable housing part. This fixing may naturally be achieved by some other method. For example, such a fixing may also be supplied by latching means or the like.

As already mentioned, however, the invention also relates to a housing-like component which can be used as a component of a nebuliser that is configured in particular according to one of the embodiments described above.

The invention starts from a housing-like component which comprises at least one coding means for clearly identifying a container that can be attached to the housing-like component, the fluid held in the container, the active substance concentration of the fluid and/or the quantity of fluid held in the container.

According to the invention, it is now proposed that the coding means be configured to be mountable, or at least replaceable, in different defined positions on or in the housing-like component.

Thus, the housing-like component can also be adapted to different codings with only one coding means. At least when the coding has to be changed there is no need to replace the entire housing-like component, only the coding means, which will also result in cost savings.

It may advantageously be envisaged that the coding means is configured in the manner of part of the wall of an imaginary hollow cylinder, the wall having at least one freely passable groove extending in the direction of an axis of symmetry of the imaginary hollow cylinder.

It is particularly convenient if the wall of the coding means comprises several, particularly four, grooves, of which only one groove is freely passable. The other grooves can then be closed off by thin transverse walls, each preferably in the form of a frangible point.

Before the manufacture of the housing-like component or before the final coding, all the grooves of the coding means are preferably closed off by the above-mentioned transverse walls. The transverse walls are expediently each located in the entry or exit region of the groove in question.

For the final coding, the transverse walls of a selected groove are removed, preferably by punching through, and the groove is thus made freely passable. The transverse walls of the other grooves still remain.

By the formation of transverse walls at both ends of the respective groove, two different codings can be obtained simply by rotating the coding means through 180 degrees.

Preferably, two coding means are provided which are, in particular, arranged offset from one another by about 180 degrees in the housing-like component. Tests have shown that such an arrangement makes it possible to achieve good stability of the housing-like component with the coding located therein.

The housing-like component may be of a very assembly-friendly design if the coding means has at least two walls, each configured in the manner of part of the wall of an imaginary hollow cylinder which are offset from one another by 180 degrees, in particular, the walls each having at least one groove extending in the direction of an axis of symmetry of the imaginary hollow cylinder and the walls being integrally connected to one another.

However, according to another feature of the invention, the coding means may be of annular configuration and has, on its end faces, openings or pin-like projections uniformly distributed around the circumference, each cooperating with pin-like projections or openings on the housing-like component, the coding means having at least one projection extending out of a plane of the annular coding means.

This is a possible method of providing the housing-like component with different coding using simple means, particularly only one coding means.

The projection is preferably rectangular in configuration and can then cooperate with a correspondingly shaped recess in a coding means in a nebuliser into which the housing-like component is to be used or inserted.

To facilitate assembly, the removable housing part has a peripheral groove and the projection has a radially outwardly directed hook-like nose for engaging in the groove.

Thus, it is ensured that the projection is fixed radially outside on the inner wall of the removable housing part and therefore cannot accidentally move radially inwards and impede the mounting of the housing-like component on a nebuliser. Thanks to the groove provided around the inner wall of the housing-like component it is easy to secure the projection radially in any rotational position (coding) of the coding element.

Expediently, a container holding a specific medicament or a specific active substance is connected to the housing-like component in fixed manner, i.e. so as to be releasable only by means of a special tool, and is thus embodied as a clearly coded retail unit that cannot be mistaken for another.

The housing parts of the nebuliser and the removable housing part are preferably made of plastics by injection moulding. Preferably, polybutylene terephthalate (PBT) or acrylonitrile-butadiene-styrene copolymer (ABS) can be used for this.

Preferred embodiments of the invention are illustrated in the drawings and described in more detail in the description that follows. Identical reference numerals refer to identical, comparable or functionally similar components.

BRIEF DESCRIPTION OF THE DRAWINGS

The drawings schematically show.

In the figures the same reference numerals are used for identical or similar parts, where corresponding or comparable properties and advantages are obtained even though the description has not been repeated.

DETAILED DESCRIPTION OF THE INVENTION

Figure 1:
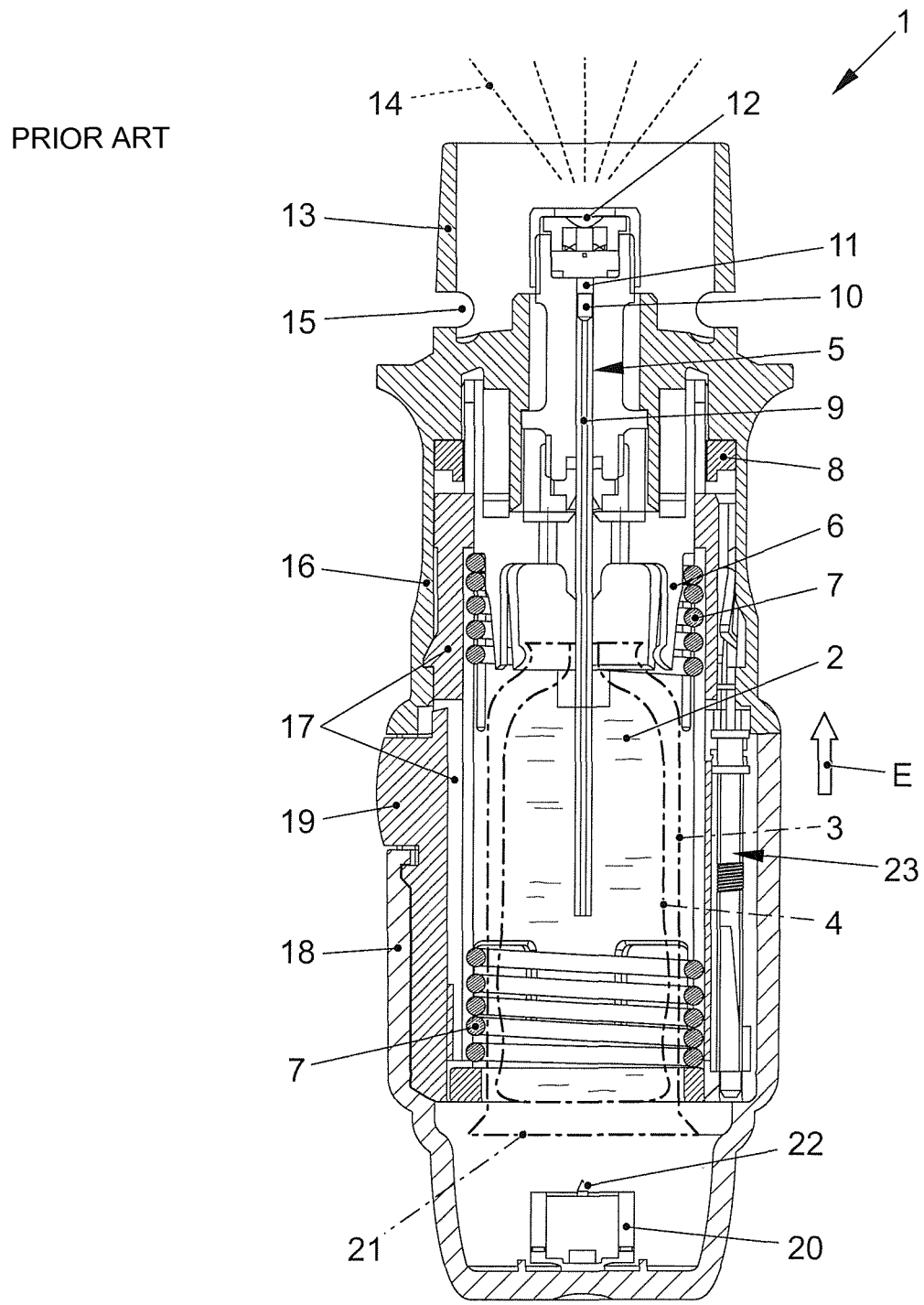
FIG. 1 a longitudinal section through a known nebuliser in the untensioned state, FIG. 2 a longitudinal section through the known nebuliser in the tensioned state, rotated through 90 degrees compared with FIG. 1, FIG. 3 a perspective view of a proposed removable housing part with an active substance container which can be inserted in a proposed nebuliser, FIG. 4 a partial perspective view of a proposed nebuliser on which the housing-like component according to FIG. 3 can be mounted, FIG. 5 a longitudinal section through a proposed nebuliser with a releasable lower housing part already fitted, FIG. 6 a perspective detailed view of a coding means used in the proposed releasable lower housing part, FIG. 7 a representation of the coding means according to view VII in FIG. 6, FIG. 8 a perspective representation of two coding means mounted on the proposed nebuliser according to FIG. 4 (upper housing part), FIG. 9 the perspective view of a proposed releasable lower housing part according to a second embodiment, FIG. 10a to c the lower housing part according to FIG. 9 in a perspective view, showing different positions of the coding element, FIG. 11 a perspective sectional view of the lower housing part according to FIG. 9 but without a container, FIG. 12a to c a perspective partial view of a proposed nebuliser on which the lower housing part according to FIG. 9 can be mounted, having a sleeve-like coding means, in different positions, FIG. 13 a perspective view of a proposed nebuliser with the lower housing part fitted thereon, in a third embodiment, FIG. 14 a perspective detailed view of the coding means used in the upper housing part or in the lower housing part of the proposed nebuliser according to FIG. 13, FIG. 15 a partial section through the embodiment shown in FIG. 13, taken along sectional view XV, and FIG. 16 a sectional view rotated through 90 degrees in relation to FIG. 15.
Figure 2:
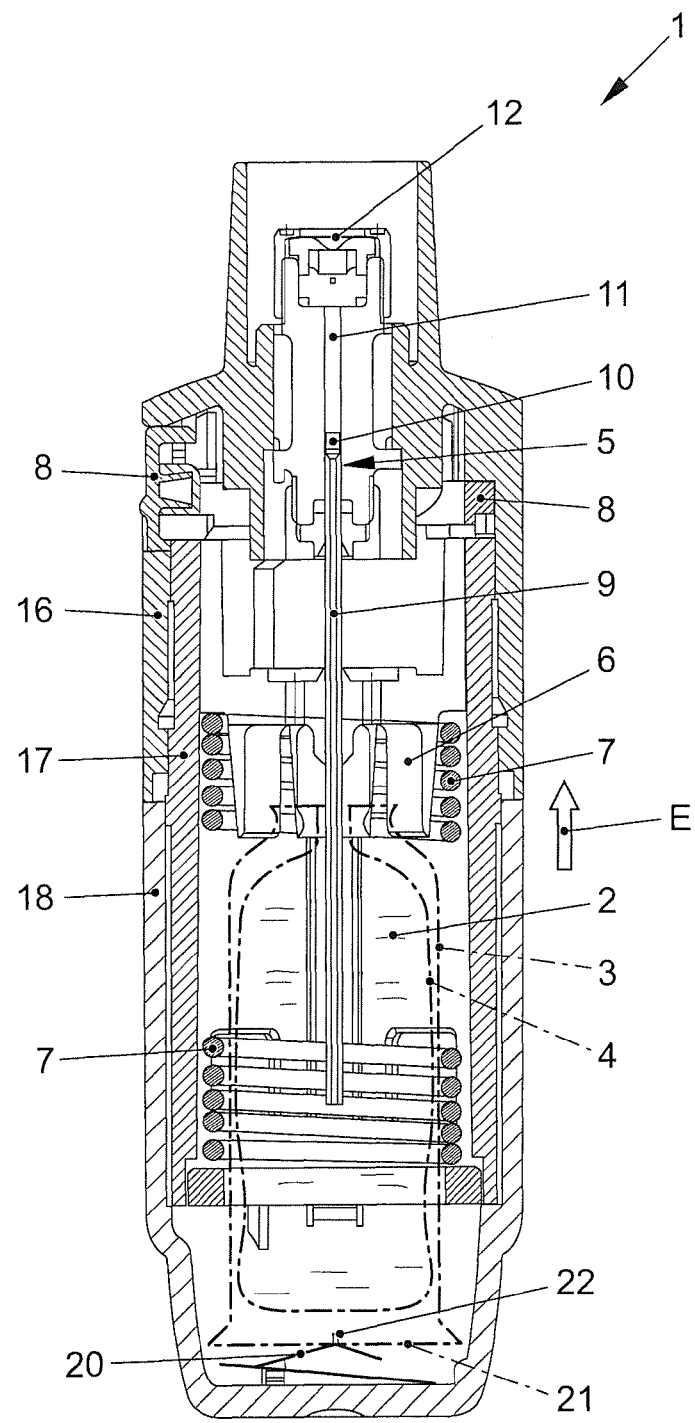

FIGS. 1 and 2 show a known nebuliser 1 for nebulising a fluid 2, particularly a highly effective medicament or the like, in a schematic view in the non-tensioned state (FIG. 1) and in the tensioned state (FIG. 2). The nebuliser 1 is embodied in particular as a portable inhaler and preferably operates without any propellant gas.

When the fluid 2, preferably a liquid, more particularly a medicament, is nebulised, an aerosol is formed that can be breathed in or inhaled by a user (not shown). Usually the inhalation takes place at least once a day, particularly several times a day, preferably at predetermined time intervals.

The nebuliser 1 has an insertable and preferably replaceable container 3 holding the fluid and forming a reservoir for the fluid 2 that is to be nebulised. Preferably, the container 3 contains sufficient fluid 2 for multiple applications, particularly for a predetermined administration period such as one month, or for at least 50, preferably at least 100 doses or sprays.

The container 3 is substantially cylindrical or cartridge-shaped and can be inserted, and optionally replaced, in the nebuliser 1 after the latter has been opened. It is preferably of rigid construction, the fluid 2 preferably being held in a bag 4 within the container 3.

The nebuliser 1 comprises a pressure generator 5 for conveying and nebulising the fluid 2, particularly in a predetermined, optionally adjustable dosage amount. The pressure generator 5 has a holder 6 for the container 3, an associated drive spring 7 (only partly shown) having a blocking element 8 that can be manually operated to release it, a conveying tube 9 with a non-return valve 10, a pressure chamber 11 and an expulsion nozzle 12 in the region of a mouthpiece 13.

During the axial tensioning of the drive spring 7, the holder 6 with the container 3 and the conveying tube 9 is moved downwards, in the drawings, and fluid 2 is aspirated out of the container 3 into the pressure chamber 11 of the pressure generator 5 via the non-return valve 10. As the expulsion nozzle 12 has a very small cross-section of flow and is embodied in particular as a capillary, a throttle effect is produced that is strong enough to reliably prevent any air being sucked in at this point even without a non-return valve.

During the subsequent relaxation after actuation of the locking element 8, the fluid 2 in the pressure chamber 11 is put under pressure by the drive spring 7 moving the conveying tube 9 back upwards—i.e. by spring force—and is expelled through the expulsion nozzle 12 where it is nebulised, particularly into particles in the µm or nm range, preferably into particles destined for the lungs measuring about 5 µm, which form a cloud or jet of aerosol 14, as indicated in FIG. 1. The conveying and nebulising of the fluid 2 are thus carried out purely mechanically, i.e. without propellant gas and without electrical means.

A user (not shown) can inhale the aerosol 14, while an air supply can be sucked into the mouthpiece 13 through at least one air supply opening 15.

The nebuliser 1 comprises an upper housing part 16 and an inner part 17 which is rotatable relative thereto, on which an in particular manually operable housing part 18 is releasably fixed, particularly fitted on, preferably by means of a retaining element 19. In order to insert and/or replace the container 3, the housing part 18 can be detached from the nebuliser 1.

By manually rotating the housing part 18, the inner part 17 can be rotated relative to the upper housing part 16, by means of which the drive spring 7 can be tensioned in the axial direction by means of a gear (not shown) acting on the holder 6. During tensioning, the container 3 is moved axially downwards until the container 3 assumes an end position as shown in FIG. 2 in the tensioned state. During the nebulising process the container 3 is moved back into its original position by the drive spring 7.

The housing part 18 preferably forms a cap-like lower housing part and fits around or over a lower free end position of the container 3, with which it can be pushed in a direction of insertion E onto or into the upper housing part 16 and attached thereto. As the drive spring 7 is tensioned, the container 3 moves with its end portion (further) into the housing part 18 or towards the end face thereof, while an axially acting spring 20 arranged in the housing part 18 comes to bear on the base 21 of the container and pierces the container 3 or a base seal thereon with a piercing element 22 when the container makes contact with it for the first time, to allow air in.

The nebuliser 1 comprises a monitoring device 23 which counts the actuations of the nebuliser 1, preferably by detecting the rotation of the inner part 17 relative to the upper part 16 of the housing. The monitoring device 23 operates purely mechanically in the embodiment shown.

The construction and mode of operation of a proposed nebuliser 1 and a proposed housing-like component 18 will now be described in more detail. Reference is made to FIGS. 3 to 16. However, only the essential differences from the known nebuliser 1 shown in FIGS. 1 and 2 will be emphasised. The remarks relating to FIGS. 1 and 2 thus apply accordingly or in a supplementary capacity.

Figure 3:
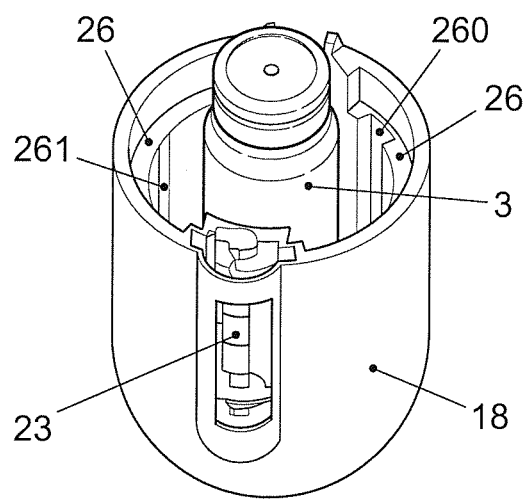
Figure 4:
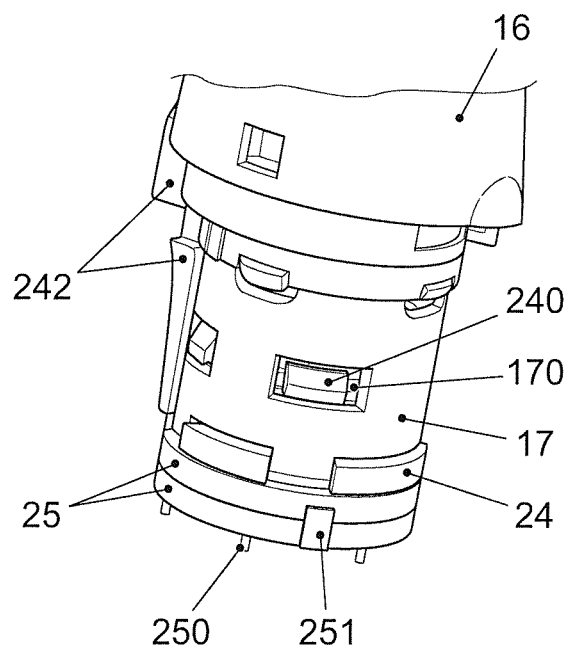
Figure 5:
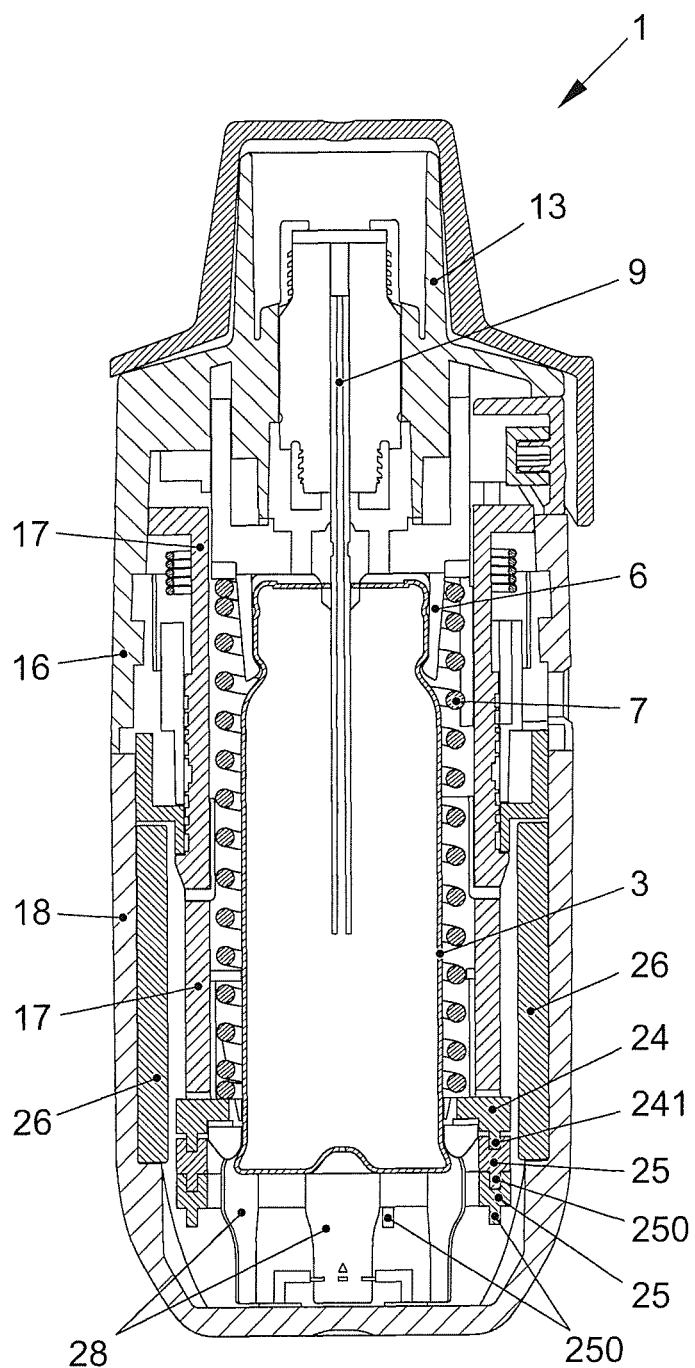

Reference will be made first to FIGS. 3 to 5.

These show a first embodiment of a proposed nebuliser 1.

The nebuliser 1 comprises an upper housing part 16 and a lower housing part 18 that can be releasably connected to the upper housing part 16.

A container 3 holding a specific active substance is already fixedly attached within the lower housing part 18, so that the lower housing part 18 forms a retail unit with the container 3.

The lower housing part 18 is provided with a monitoring device 23. In addition, the lower housing part 18 accommodates two coding means, each having a freely passable groove 260 and a plurality of grooves 261 that are not freely passable.

The form and function of the coding means 26 will be explained in more detail hereinafter.

The upper housing part 16, in return, has two identically constructed coding means 25 that are connected to a closure member 24.

Moreover, pin-like projections 250 and a radially projecting nose 251 of the coding means 25 are shown.

The closure member 24 is held in latching openings 170 of the inner part 17 by latching elements 240.

A locking and unlocking element 242 is integrally connected to the closure member 24.

The locking and unlocking element 242 can be pressed in radially and serves to lock or unlock the releasable lower housing part 18.

FIG. 5 shows that the coding means 26 abut with their outer walls on the inner wall of the lower housing part 18. As will be explained in more detail below, they cooperate with the coding means 25 attached to the upper housing part 16.

The container 3 is fixedly attached to the lower housing part 18 by a base element 28. In particular, the base element 28 comprises several, preferably four, spring-like arms which extend with their ends over a widening base region of the container 3.

Figure 6:
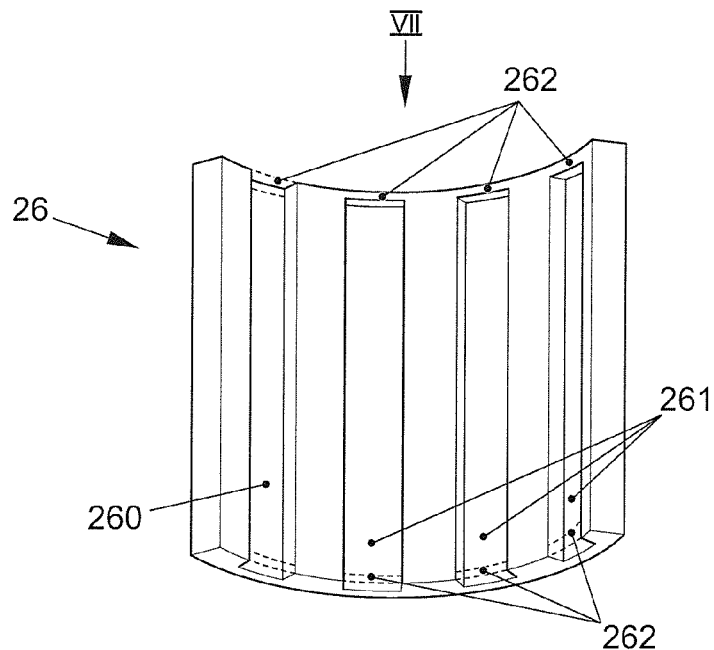

The shape and cooperation of the coding means 25 and 26 will now be explained by reference to FIGS. 6 to 8.

Figure 7:
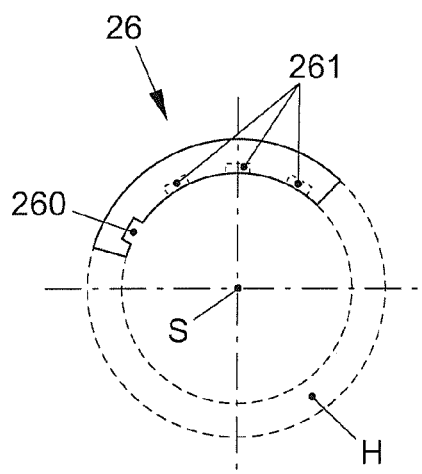

Each of the coding elements 26 is configured in the manner of part of the wall of an imaginary hollow cylinder H (cf. dashed curved lines in FIG. 7). The wall of the coding means 26 comprises four grooves 261 and 260, respectively, extending in the direction of an axis of symmetry S of the imaginary hollow cylinder H.

The groove 260 is embodied as a freely passable groove, while the grooves 261 have a transverse wall 262 at least at one end, which blocks free passage.

Figure 8:
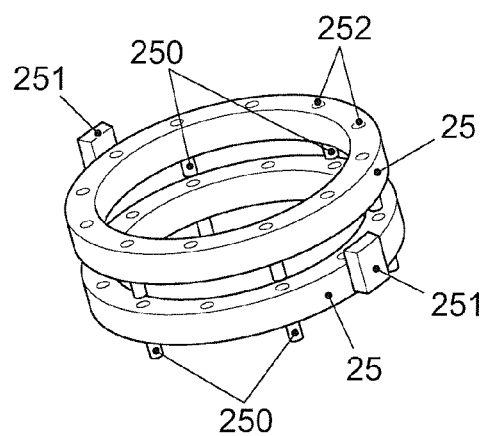
Figure 9:
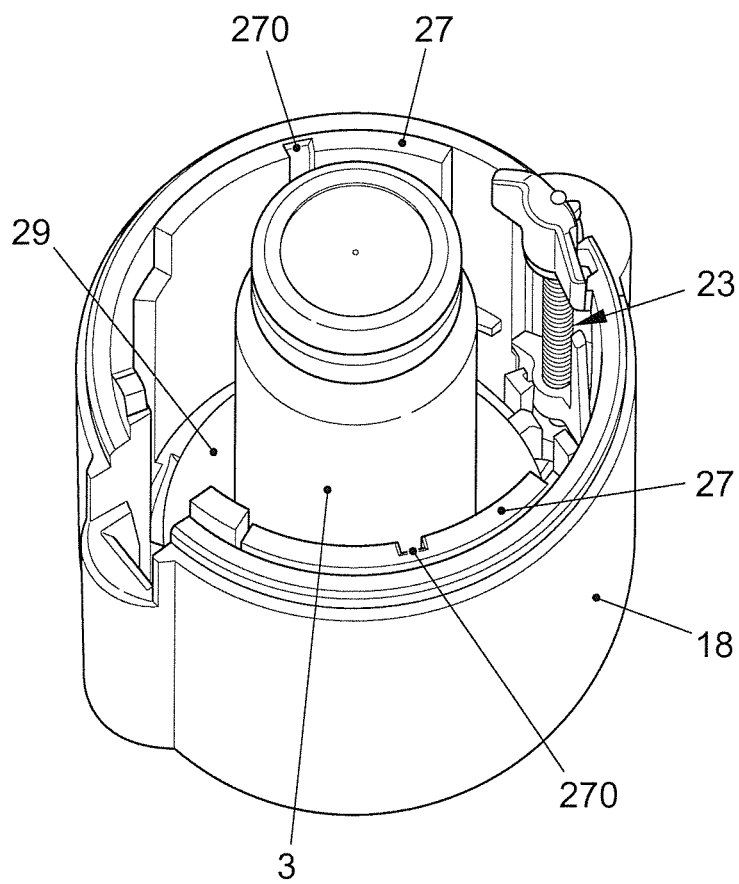

FIG. 8 is a more detailed view of the coding means 25 that are connected to the upper housing part 16.

The coding means 25 are of identical construction and are annular in shape.

The annular coding means 25 are provided with openings 252 on one end face and with pin-like projections 250 on the opposite side. The openings 252 are configured so that they are able to accommodate the pin-like projections 250, such that the coding means 25 can lie with their end faces against one another (cf. also FIGS. 4 and 5).

In addition, each coding means 25 comprises a nose 251 on its radially outer side.

It is clear that the openings 252 and also the pin-like projections 250 are distributed equidistantly over the circumference of the annular coding means 25. Preferably, twelve openings 252 are provided on one end face and six pin-like projections 250 are provided on the opposite end face. Thus the coding means 25 and hence the noses 251 can be aligned in a plurality of angular positions relative to one another.

The nose 251 is configured so that it can be accommodated in the freely passable groove 260 of the coding means 26 so as to be movable but safely guided.

In the production process, depending on the desired coding, the two coding means 25 are fitted together by their end faces and then attached to the upper housing part 16, particularly on the closure member 24 attached to the inner part 17.

Pin-like projections 241 of the closure member 24 which are provided on the end face engage in the openings 252 of the coding means 25 located above (cf. FIG. 5).

The coding means 26 are latched to the inner wall of the lower housing part 18 in a manner not shown in detail.

It should be mentioned that before the coding, the coding element 26 is configured so that all the grooves 260 and 261 are provided with the transverse walls 262 (located at the top in FIG. 6 and indicated by dashed lines below). The transverse walls 262 each preferably take the form of a kind of frangible point.

For the final coding, each coding means 26 must be provided with a freely passable groove (the groove 260 in the embodiment shown). This is done by removing both transverse walls 262 of a groove. The transverse walls of the other grooves 261 have to retain at least one transverse wall 262 which has to be aligned with the upper housing part 16 (i.e. at the top, as in FIG. 6) in the assembly position of the coding means 26, to provide a clear coding.

If both transverse walls 262 are left in place in the grooves 261 that are not freely passable (in contrast to the embodiment of FIG. 6), this also has the advantage that by swivelling the coding means 26 through 180° without any further modification a different coding can be achieved, as the freely passable groove 260 will then be in a different place.

It will be understood that by the combination of the two coding means 26 with their four respective coding options (grooves) and the two annular coding means 25, a total of 16 possible codes can be obtained. This therefore provides a high degree of flexibility.

Referring to FIGS. 9 to 12, a second embodiment of the proposed nebuliser will now be described.

A coding means 27 which comprises at least two walls each configured in the manner of part of the wall of an imaginary hollow cylinder (comparable with the coding means 26 in FIG. 6) is inserted in the releasable lower housing part 18.

In this embodiment, the lower housing part 18 is also already fixedly connected to a container 3 as a retail unit, the container 3 additionally being radially supported via an annular support element 29.

The walls of the coding means 27 are preferably offset from one another by about 180 degrees, the walls each having at least one groove 270 extending in the direction of insertion of the container 3.

Figure 11:
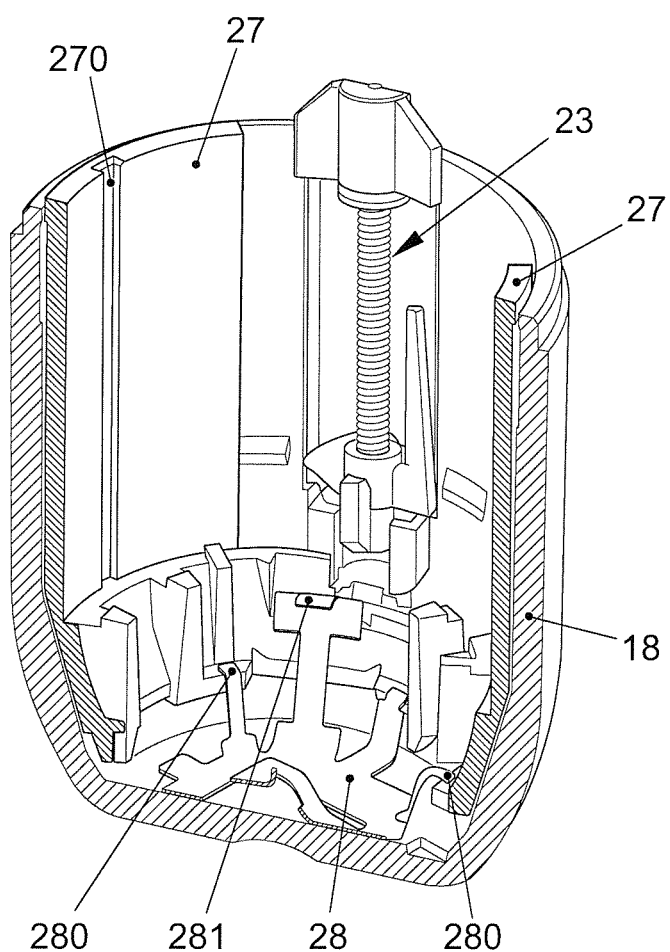

The walls are integrally connected to one another, as is clear particularly from FIG. 11.

This figure clearly also shows the base element 28 which serves to attach the container 3 at its base by means of radially inwardly bent arms 281.

Radially outwardly bent arms 280 engage behind the base region of the coding means 27 and hold the latter securely in the lower housing part 18 so that they cannot get lost. In the embodiment shown, the grooves 270 are also offset from one another by about 180 degrees.

As can be seen from FIG. 10 in particular, the two walls of the coding means 27 are provided in the lower region with elongate groove-like indentations 271. Preferably, seven such indentations 271 are provided.

By contrast, the lower housing part 18 comprises, on its inner wall, in the region of the indentations 271, at least one elongate bulge (not shown in detail) which may correspond to at least one of the elongate indentations 271.

Obviously, it is also possible to provide indentations on the lower housing part 18 and bulges on the walls of the coding means 27.

It will readily be understood that the coding element 27 may thus assume seven possible clearly defined positions.

Figure 10A:
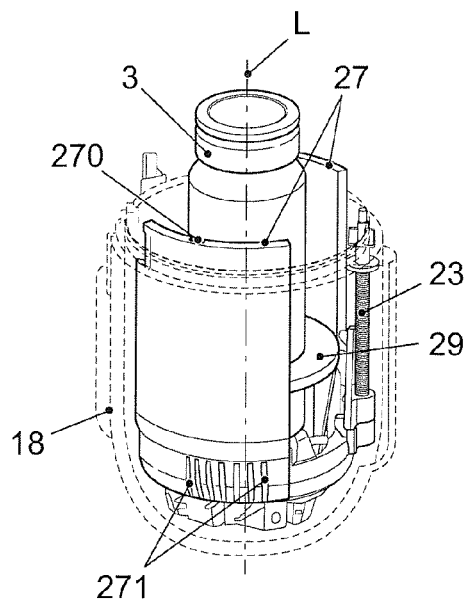
Figure 10B:
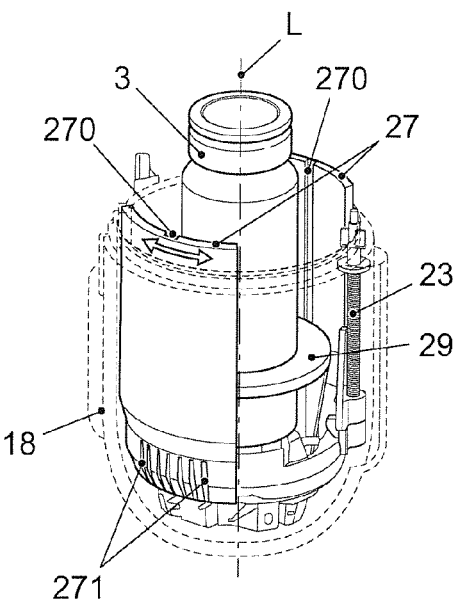
Figure 10C:
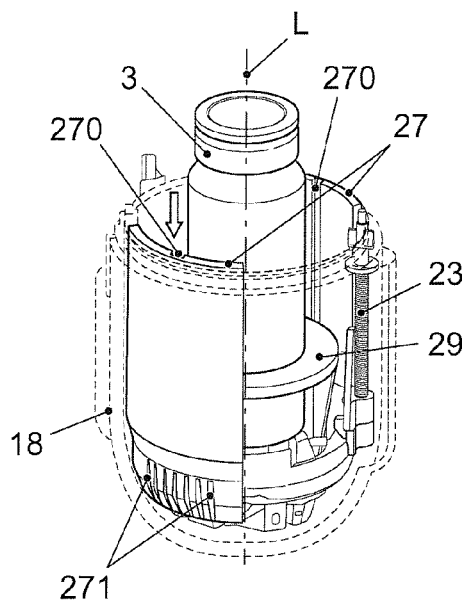

FIGS. 10a to c show how easy it is to fix the final coding of the lower housing part 18 in the manufacturing process.

Thus the lower housing part 18 is in an uncoded state in FIG. 10a. The coding means 27 project from the lower housing part 18 to such an extent that the elongate indentations 271 of the coding means 27 are not in engagement with the elongate bulges in the lower housing part 18.

Therefore the coding means 27 is freely rotatable over a specific angular range about a longitudinal axis L of the container 3 or the lower housing part 18.

In accordance with the seven elongate bulges 271 provided, one of these seven possible positions can thus be selected by free rotation.

In FIG. 10b a possible position has been selected by rotation to the left, a final fixing or coding then being obtained by pushing or pressing the coding means 27 into the lower housing part 18 by the cooperation of the elongate indentations 271 with elongate bulges on the lower housing part 18 (FIG. 10c).

Figure 12A:
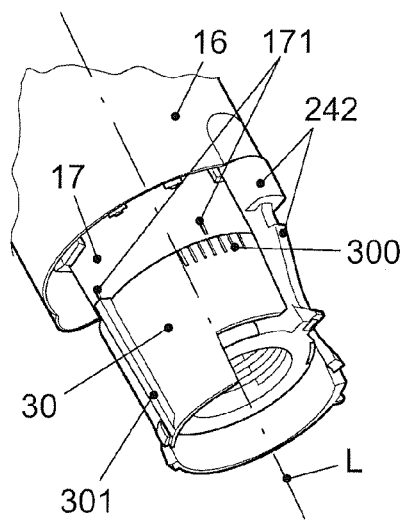
Figure 12B:
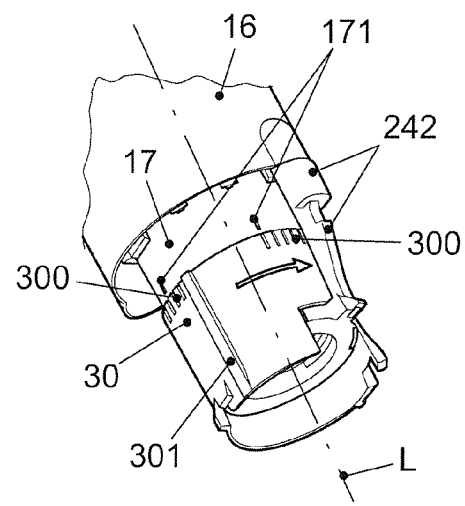
Figure 12C:
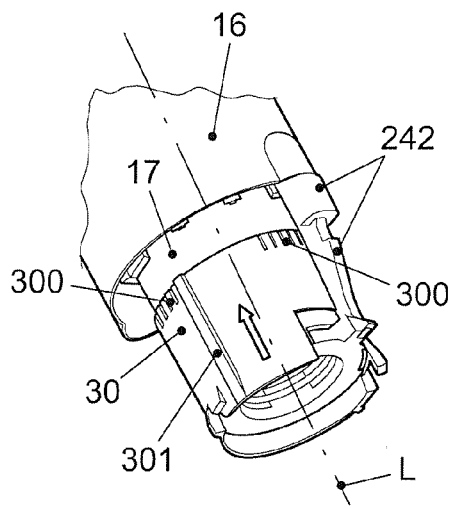
Figure 13:
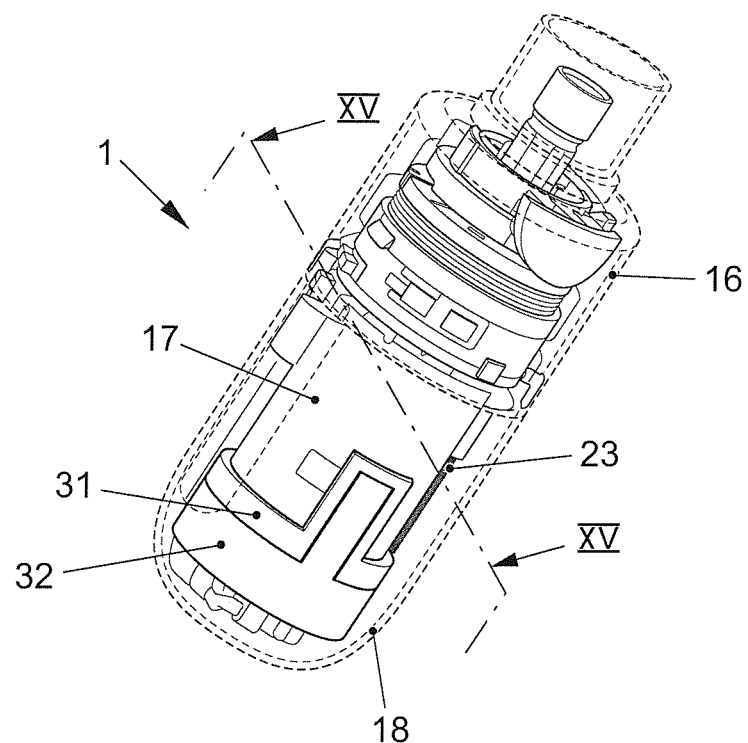

FIGS. 12a to c show the upper housing part 16 corresponding to this embodiment by way of example.

The upper housing part 16 is provided with a sleeve-like coding means 30.

The sleeve-like coding means 30 is pushed over the inner part 17 of the upper housing part 16.

In accordance with the coding on the lower housing part 18 as described above, a final coding can also be produced very late in the manufacturing process with the upper housing part 16 as well.

Thus FIG. 12a shows the coding means 30 in a neutral position in which it has not yet been coded and in particular is still freely rotatable relative to the inner part 17 over a certain angular range about its longitudinal axis L.

In particular, an interstice is thus formed between the locking and unlocking element 242 and the inner part 17 such that the rotation of the coding means 30 is unimpeded.

The coding means 30 also comprises two rib-like projections 301 preferably offset by 180 degrees which are configured to engage in the grooves 270 of the coding means 27 of the upper housing part 18.

The coding means 30, preferably uniformly distributed at four points around the circumference, are also provided with seven elongate recesses 300. The recesses 300 are embodied so as to cooperate with corresponding elongate projections 171 on the inner part 17 which are arranged on the inner part 17, preferably offset by 90° around the circumference.

In FIG. 12b the coding means 30 has been rotated to the right from its neutral position into a possible final position and then in FIG. 12c pushed further onto the inner part, so that one of the elongate recesses 300 can cooperate with one of the elongate projections 171 and thus fix the coding of the upper housing part 16 as well.

Thus, seven possible codes can be produced easily using identical components.

Finally, a third embodiment of the proposed nebuliser 1 will be described with reference to FIGS. 13 to 16.

The coding of the nebuliser 1 has only two annular coding elements 31 and 32 in this embodiment.

Figure 14:
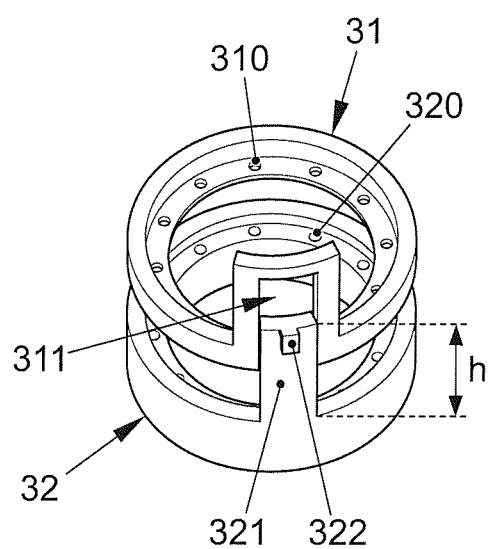

The annular coding elements 31 and 32 are described in more detail in FIG. 14.

It is apparent that the coding elements 31 and 32 each have a substantially L-shaped cross-section, the coding element 31 preferably having twelve through-openings 310 on the end face (i.e. located in the horizontal region of the arm of the L), which are distributed equidistantly over the circumference.

Similarly, the coding element 32 preferably has twelve through-openings 320 on its end face, distributed equidistantly over the circumference.

For matching the code, the coding means 32 is provided with a rectangular projection 321 which extends in a direction of insertion E (cf. FIG. 15) of the container 3 towards the upper housing part 16 or the inner part 17.

In corresponding manner the coding means 31 is provided with a rectangular recess 311 which is configured so that it can cooperate in mating manner with the projection 321.

Figure 15:
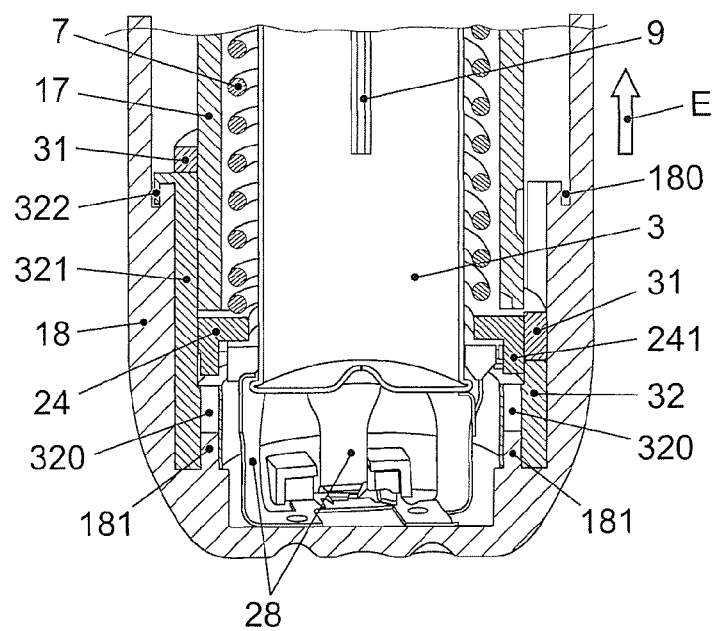
Figure 16:
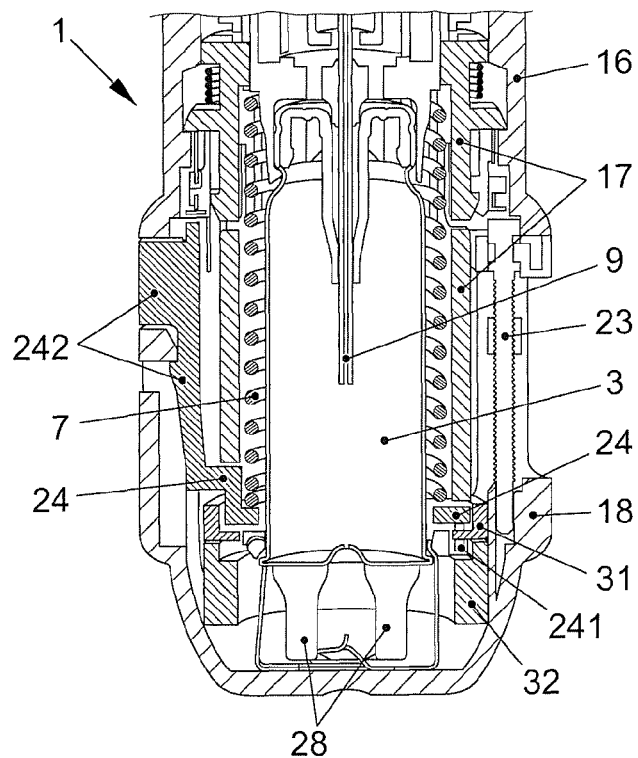

FIGS. 15 and 16 in particular show that the coding means 31 is connected to the upper housing part 16 and the coding means 32 is connected to the lower housing part 18.

Specifically, the coding means 31 with its through-openings 310 in a selection position is pushed onto the pin-like projections 241 of the closure member 24 (in comparable manner to the upper ring 25 in FIG. 5), the closure member 24 having been attached to the inner part 17 of the upper housing part 16.

The coding means 31 are thus fixed in a defined position.

The coding means 32 are pushed onto pin-like projections 181 of the lower housing part 18 by means of the through-openings 320 and thus held in a defined position as well.

The rectangular projection 321 is additionally provided, at its upper end, with a radially outwardly directed nose 322 which, in the assembly position of the coding means 32, engages behind a radially encircling groove 180 of the lower housing part 18.

Thus the projection 321 is securely held in the lower housing part 18 without being able to shift radially inwards and prevent the lower housing part 18 and upper housing part 16 from being joined together when their codes match.

If the codes do not match, i.e. if the projection 321 on the one hand and the recess 311 on the other hand in the lower housing part 18 and upper housing part 16, respectively, are each in a different angular position, it is not possible to fit the housing parts 16 and 18 together completely.

In particular, the projection 321 has a height h which is such that the conveying tube 9 contained in the upper housing part 16 cannot pass far enough into the container 3 to cause contamination of the conveying tube 9 with the active substance held in the container 3.

Both the pin-like projections 241 of the closure member 24 which is annular in this region, and the pin-like projections 181 of the lower housing part 18 are distributed equidistantly around the circumference in the same way as the through-openings 310 and 320. Thus the coding means 31 and 32 can be mounted in defined manner in a number of different positions in the upper housing part 16 and in the lower housing part 18.

The embodiments described hereinbefore, especially individual elements and aspects of the embodiments, may be combined with one another and/or reversed in their kinematic operation, as necessary. In particular, the number and arrangement of the defined selectable positions of the coding means may be varied as necessary and adapted to the particular conditions.

LIST OF REFERENCE NUMERALS 1 nebulizer
2 fluid
3 container
4 bag
5 pressure generator
6 holder
7 drive spring
8 blocking element
9 conveying tube
10 non return valve
11 pressure chamber
12 expulsion nozzle
13 mouthpiece
14 aerosol
15 air supply opening
16 upper housing part
17 inner part
170 latching openings
171 elongate projections
18 releasable housing part (lower part)

180 encircling groove
181 pin-like projections
19 retaining element
20 spring (in lower housing part)
21 container base
22 piercing element
23 monitoring device
24 closure member with latching elements for securing
240 latching element
241 pin-like projections
242 locking and unlocking element
25 annular coding means
250 pin-like projections
251 nose
252 openings
26 coding means in the removable housing part
260 freely passable groove
261 non-freely passable groove
262 transverse walls
27 coding means in the removable housing part
270 groove
271 elongate indentations
28 base element
280 outwardly bent arms
281 inwardly bent arms
29 annular support element
30 sleeve-like coding means
300 elongate recesses
301 rib-like projection
31 annular coding means
310 through-opening
311 rectangular recess
32 annular coding means
320 through-opening
321 rectangular projection
322 nose
E direction of insertion or introduction of the container into the upper or lower housing part
h height of the projection
H hollow cylinder
L longitudinal axis
S axis of symmetry of the hollow cylinder

What is claimed is:

1. A portable inhaler (1) for a liquid (2), into which a container (3) holding the liquid (2) can be inserted, wherein the inhaler (1) has
a pressure generator (5) for nebulizing the liquid (2) to form an inhalable aerosol suitable for administration of a medicament wherein the pressure generator comprises a drive spring, and
a housing part (18) which is removable from the inhaler (1) for the replacement of the container (3), wherein the container (3) is connected to the housing part (18) in fixed manner,
wherein the inhaler comprises first coding component (25;30;31) which first coding component is in the form of one or more projections and the housing part (18) comprises second coding component (26;27;32) which second coding component is in the form of one or more grooves or indentations, wherein the first coding component (25;30;31) and the second coding component (26;27;32) cooperate such that the container (3) can only be inserted into the portable inhaler (1) or used therewith when the first coding component (25;30;31) and the second coding component (26;27;32) have matching codes and the first coding component can be inserted into the second coding component,
wherein at least one of the first coding component (25;30;31) and the second coding component (26;27;32) can be mounted in different positions such that in each position a different coding is obtained in which the first coding component (25;30;31) and the second coding component (26;27;32) match one another.

2. The portable inhaler (1) according to claim 1, characterised in that the second coding component (26) associated with the removable housing part (18) is configured in the manner of part of the wall of an imaginary hollow cylinder (H), the wall having at least one freely passable groove (260) extending in the direction of an axis of symmetry (S) of the imaginary hollow cylinder (H), and the first coding component (25) associated with the portable inhaler (1) is of ring-like configuration, with at least one nose-like projection (251) for displaceable engagement in the groove (260), the ring-like first coding component (25) comprising a plurality of openings (252) on one end face and a plurality of pin-like projections (250) on an opposite end face.

3. The portable inhaler (1) according to claim 2, characterised in that the second coding component (26) associated with the removable housing part (18) comprises a plurality of grooves (260,261), of which one groove (260) is freely passable and the other grooves (261) are blocked in their continuity by transverse walls (262).

4. The portable inhaler (1) according to claim 2, characterised in that two second coding components (26) are associated with the removable housing part (18) and two first coding components (25) are associated with the portable inhaler (1).

5. The portable inhaler (1) according to claim 1, characterised in that the second coding component (27) associated with the removable housing part (18) comprises at least two walls each configured in the manner of part of the wall of an imaginary hollow cylinder, which are offset from one another by about 180°, the walls each having at least one groove (270) extending in the direction of insertion of the container (3) and the walls being integrally connected to one another and the first coding component (30) associated with the portable inhaler (1) being of sleeve-like configuration, while the walls of the second coding component (27) associated with the removable housing part (18) radially surround, at least in parts, the first coding component (30) associated with the portable inhaler (1) and at the same time guide means (270,301) for both the first and second coding components (27,30) engage with one another.

6. The portable inhaler (1) according to claim 5, characterised in that the second coding component (27) associated with the removable housing part (18) can be brought into a position in which it can be rotated freely within the housing part (18) at least over a limited angular range and by further insertion into the housing part (18) can be moved into a position in which it is no longer rotatable.

7. The portable inhaler (1) according to claim 5, characterised in that the first coding component (30) associated with the portable inhaler (1) can be brought into a position in which it is freely rotatable on the portable inhaler (1) at least over a limited angular range and by being pushed further onto the portable inhaler (1) can be moved into a position in which it is no longer rotatable.

8. The portable inhaler (1) according to claim 1, characterised in that both the first and the second coding components (31,32) with an annular outline are provided, each of which has openings (310, 320) or pin-like projections on their end faces, uniformly distributed about the circumference, which cooperate respectively with pin-like projections (241, 181) or openings provided on the portable inhaler (1)

or the removable housing part (18), the second coding component (32) associated with the removable housing part (18) having at least one projection (321) extending in the direction of insertion (E) of the container (3) and the first coding component (31) associated with the portable inhaler (1) having at least one recess (311) extending in the direction of insertion (E) of the container (3) which is configured to receive the projection (321).

9. The portable inhaler (1) according to claim 8, characterised in that the removable housing part (18) comprises an encircling groove (180) and the projection (321) of the second coding component (32) has a radially outwardly directed hook-like nose (322) for engaging in the groove (180).

10. The portable inhaler (1) according to claim 1, characterized in that the first coding component (25;30;31) can be mounted on the portable inhaler (1) in different positions and that the second coding component (26;27;32) can be mounted on the removable housing part (18) in different defined positions.

\* \* \* \* \*